US011756675B2

(12) United States Patent
Orringer et al.

(10) Patent No.: US 11,756,675 B2
(45) Date of Patent: Sep. 12, 2023

(54) SYSTEMS AND METHODS FOR ANALYSIS AND REMOTE INTERPRETATION OF OPTICAL HISTOLOGIC IMAGES

(71) Applicants: THE REGENTS OF THE UNIVERSITY OF MICHIGAN, Ann Arbor, MI (US); INVENIO IMAGING, INC., Santa Clara, CA (US)

(72) Inventors: Daniel Orringer, Ann Arbor, MI (US); Balaji Pandian, Farmington Hills, MI (US); Christian Freudiger, San Carlos, CA (US); Todd Hollon, Ann Arbor, MI (US)

(73) Assignees: THE REGENTS OF THE UNIVERSITY OF MICHIGAN, Ann Arbor, MI (US); INVENIO IMAGING, INC., Santa Clara, CA (US)

( * ) Notice: Subject to any disclaimer, the term of this patent is extended or adjusted under 35 U.S.C. 154(b) by 37 days.

(21) Appl. No.: 16/967,052

(22) PCT Filed: Feb. 6, 2019

(86) PCT No.: PCT/US2019/016886
§ 371 (c)(1),
(2) Date: Aug. 3, 2020

(87) PCT Pub. No.: WO2019/157078
PCT Pub. Date: Aug. 15, 2019

(65) Prior Publication Data
US 2021/0050094 A1    Feb. 18, 2021

Related U.S. Application Data

(60) Provisional application No. 62/627,033, filed on Feb. 6, 2018.

(51) Int. Cl.
*G06K 9/00* (2022.01)
*G16H 30/40* (2018.01)
(Continued)

(52) U.S. Cl.
CPC ............ *G16H 30/40* (2018.01); *G01N 21/65* (2013.01); *G06N 3/08* (2013.01); *G06T 7/0012* (2013.01);
(Continued)

(58) Field of Classification Search
CPC .. G16H 30/40; G01N 21/65; G01N 2021/655; G06N 3/08; G06T 7/0012;
(Continued)

(56) References Cited

U.S. PATENT DOCUMENTS

2010/0280762 A1*  11/2010  Maier ................. G02B 21/365
                                                        702/19
2010/0304989 A1   12/2010  Von Hoff et al.
(Continued)

FOREIGN PATENT DOCUMENTS

CN       103582455 A      2/2014
CN       106030608 A     10/2016
(Continued)

OTHER PUBLICATIONS

Ozeki, Yasuyuki, et al. "High-speed molecular spectral imaging of tissue with stimulated Raman scattering." Nature photonics 6.12 (2012): 845-851. (Year: 2012).*
(Continued)

*Primary Examiner* — Jonathan S Lee
(74) *Attorney, Agent, or Firm* — Harness, Dickey & Pierce, P.L.C.

(57) ABSTRACT

A system is presented for analyzing and interpreting histologic images. The system includes an imaging device and a diagnostic module. The imaging device captures an image of
(Continued)

a tissue sample at an optical section of the tissue sample, where the tissue sample has a thickness larger than the optical section. The system may further include an image interpretation subsystem located remotely from the imaging device and configured to receive the images from the imaging device. The diagnostic module is configured to receive the images for the tissue sample from the imaging device and generates a diagnosis for the tissue sample by applying a machine learning algorithm to the images. The diagnostic module may be interface directly with the imaging device or located remotely at the image interpretation subsystem.

22 Claims, 23 Drawing Sheets

(51) Int. Cl.
    *G01N 21/65*         (2006.01)
    *G06N 3/08*          (2023.01)
    *G06T 7/00*          (2017.01)
(52) U.S. Cl.
    CPC ............... *G01N 2021/655* (2013.01); *G06T 2207/10061* (2013.01); *G06T 2207/20081* (2013.01); *G06T 2207/20084* (2013.01); *G06T 2207/30016* (2013.01); *G06T 2207/30096* (2013.01)
(58) Field of Classification Search
    CPC . G06T 2207/10061; G06T 2207/20081; G06T 2207/20084; G06T 2207/30016; G06T 2207/30096
    USPC ........................................................ 382/128
    See application file for complete search history.

(56) References Cited

U.S. PATENT DOCUMENTS

| | | | |
|---|---|---|---|
| 2016/0035093 A1 | 2/2016 | Kateb et al. | |
| 2017/0356053 A1 | 12/2017 | Otto et al. | |
| 2020/0279368 A1* | 9/2020 | Tada | G06T 7/0012 |
| 2020/0372635 A1* | 11/2020 | Veidman | G16H 50/20 |

FOREIGN PATENT DOCUMENTS

| | | |
|---|---|---|
| JP | H10-197522 A | 7/1998 |
| JP | 2000057349 A | 2/2000 |
| JP | 2001188906 A | 7/2001 |
| JP | 2008204432 A | 9/2008 |
| JP | 20128027 A | 1/2012 |
| JP | 201640650 A | 3/2016 |
| JP | 2017003311 A | 1/2017 |
| JP | 2017187409 A | 10/2017 |
| WO | WO-2014063257 A1 | 5/2014 |
| WO | WO-2014192876 A1 | 12/2014 |
| WO | WO-2016142533 A1 | 9/2016 |
| WO | WO-2019026081 | 2/2019 |

OTHER PUBLICATIONS

Ji, Minbiao, et al. "Detection of human brain tumor infiltration with quantitative stimulated Raman scattering microscopy." Science translational medicine 7.309 (2015): 309ra163-309ra163. (Year: 2015).*
Potts, William JE. "Generalized additive neural networks." Proceedings of the fifth ACM SIGKDD international conference on Knowledge discovery and data mining. 1999. (Year: 1999).*
Lu, Fa-Ke, et al. "Label-Free Neurosurgical Pathology with Stimulated Raman ImagingLabel-Free Neurosurgical Pathology with SRS Imaging." Cancer research 76.12 (2016): 3451-3462. (Year: 2016).*
Desroches, Joannie, et al. "A new method using Raman spectroscopy for in vivo targeted brain cancer tissue biopsy." Scientific reports 8.1 (2018): 1-10. (Year: 2018).*
Yang Yifan et al: "Stimulated Raman scattering microscopy for rapid brain tumor histology", Journal of Innovative Optical Health Sciences, vol. 10, No. 05, Aug. 23, 2017, pp. 1730010-1, XP055866412.
Xu Yan et al: "Deep convolutional activation features for large scale Brain Tumor histopathology image classification and segmentation", 2015 IEEE International Conference on Acoustics, Speech and Signal Processing (ICASSP), IEEE, Apr. 19, 2015, pp. 947-951, XP033186855.
Anonymous: "Convolutional Neural Network", Wikipedia, Feb. 4, 2018, XP055867035.
Orringer, Daniel A., et al. "Rapid intraoperative histology of unprocessed surgical specimens via fibre-laser-based stimulated Raman scattering microscopy," *Nature Biomedical Engineering*, 1, 0027, (Feb. 6, 2017); DOI: 10.1038/s41551-016-0027.
Ji, Minbio et al "Detection of Human Brain Tumor Infiltration With Quantitative Stimulated Raman Scattering Microscope", www.ScienceTranslational Medicine.Org (Oct. 2015) vol. 7, Issue 309 309ra163.
International Search Report and Written Opinion of the International Searching Authority, issued in PCT/US2019/016886, dated Jun. 21, 2019; ISA/US.
Orringer et al., Rapid intraoperative histology of unprocessed surgical specimens via fibre-laser-based stimulated Raman scattering microscopy, Nature Biomedical Engineering, Feb. 6, 2017, vol. 1/No. 27, pp. 1-13.
Japanese Office Action regarding Application No. 2020542587, dated Jun. 29, 2022.
European Office Action from counterpart EP197513575, dated Jul. 4, 2023.

* cited by examiner

Raw Image

Noise Corrected Image

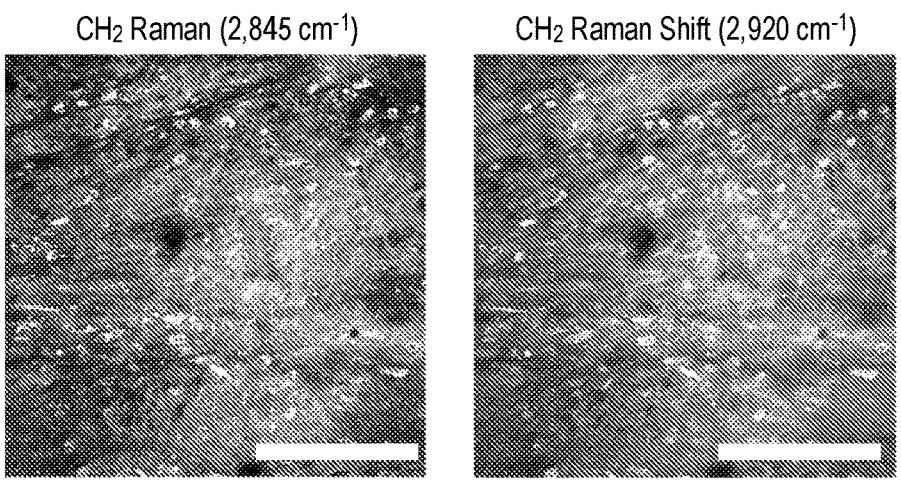
CH₂ Raman (2,845 cm⁻¹)  CH₂ Raman Shift (2,920 cm⁻¹)
FIG. 4A   FIG. 4B
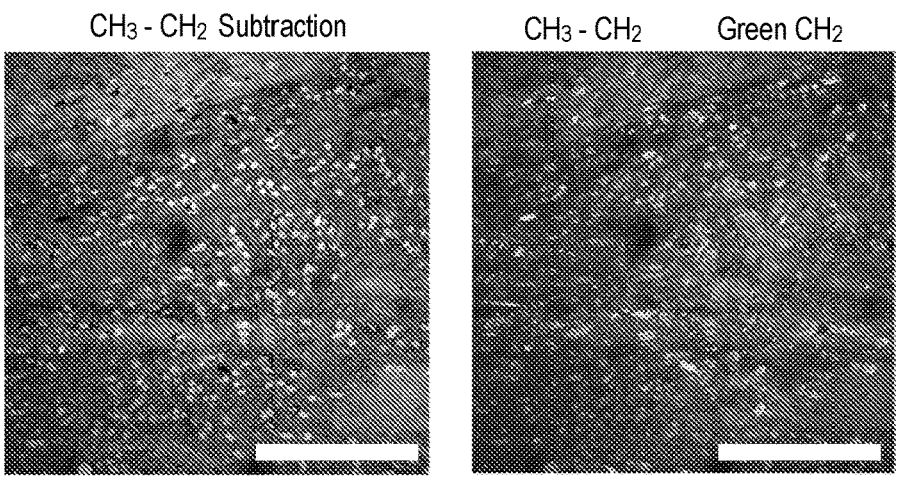
CH₃ - CH₂ Subtraction   CH₃ - CH₂   Green CH₂
FIG. 4C   FIG. 4D
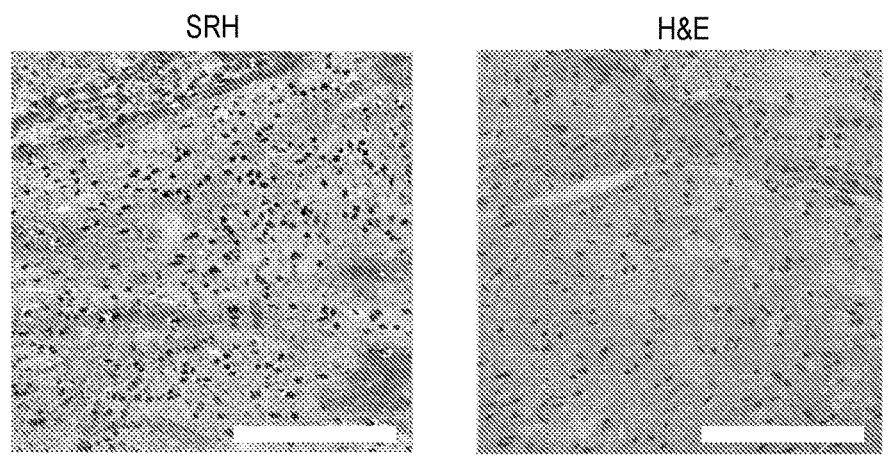
SRH   H&E
FIG. 4E   FIG. 4F

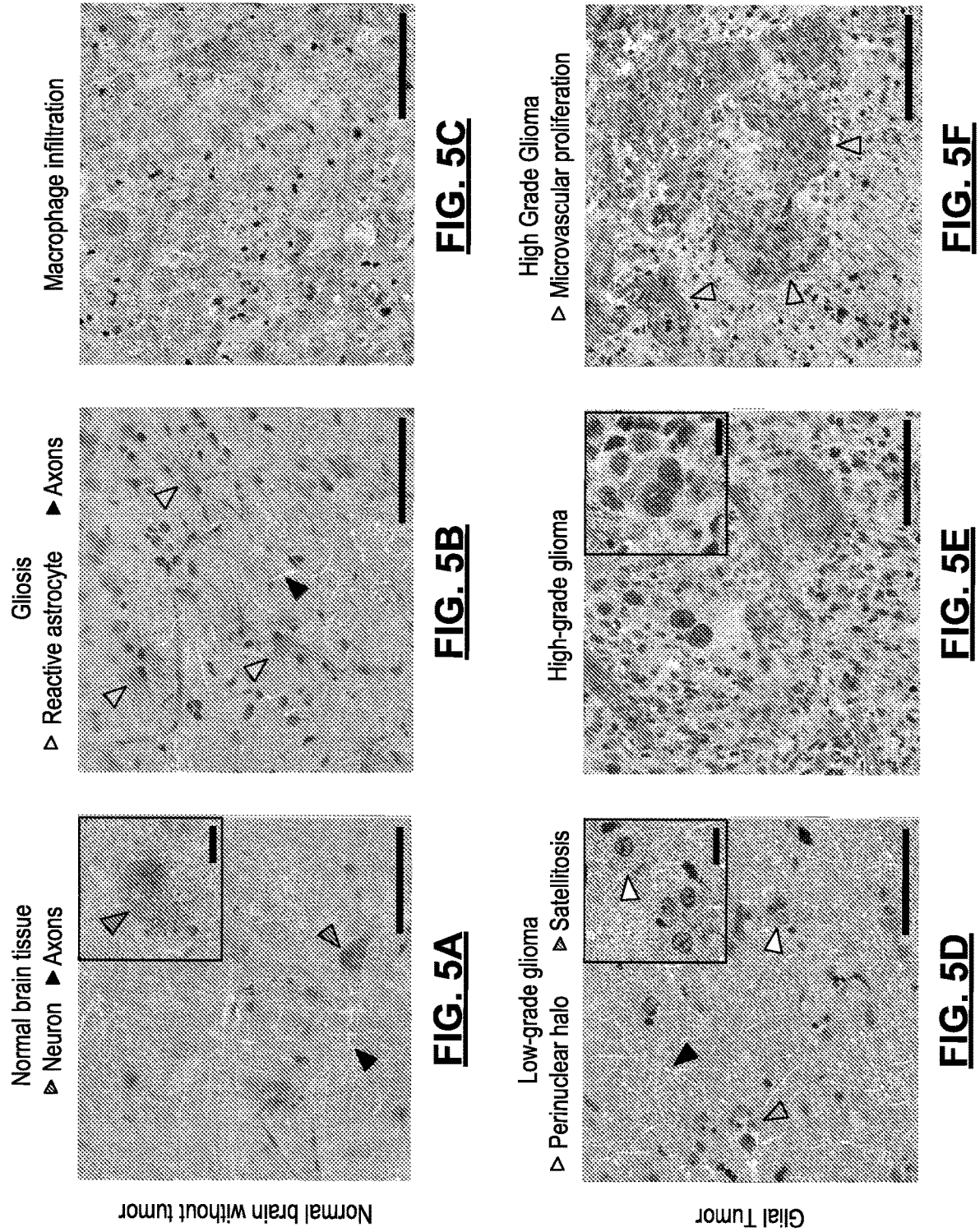

Principal of Stitched Image Acquisition

SYSTEMS AND METHODS FOR ANALYSIS AND REMOTE INTERPRETATION OF OPTICAL HISTOLOGIC IMAGES

CROSS-REFERENCE TO RELATED APPLICATIONS

This application is a U.S. National Phase Application under 35 U.S.C. 371 of International Application No. PCT/US2019/016886 filed on Feb. 6, 2019, which claims the benefit of U.S. Provisional Application No. 62/627,033 filed on Feb. 6, 2018. The entire disclosures of the above applications are incorporated herein by reference.

GOVERNMENT CLAUSE

This invention was made with government support under CA226527, EB017254, and CA206664 awarded by the National Institutes of Health. The government has certain rights in the invention.

FIELD

The present disclosure relates to systems and methods for the analysis and remote interpretation of histologic images and, more particularly, to systems and methods for analyzing and interpreting Stimulated Raman Scattering (SRS) images of tissue.

BACKGROUND

The optimal surgical management of brain tumors varies widely depending on histologic subtype. Though some tumors of the central nervous system (CNS) have a distinct gross appearance, others are difficult to differentiate. Consequently, the importance of intraoperative histopathologic diagnosis in brain tumor surgery has been recognized for over 85 years.

Existing intraoperative histologic techniques, including frozen sectioning and cytologic preparations, require skilled technicians and clinicians working in surgical pathology laboratories to produce and interpret slides. However, the number of centers where brain tumor surgery is performed exceeds the number of board-certified neuropathologists, eliminating the possibility for expert intraoperative consultation in many cases. Even in the most advanced, well-staffed hospitals, turnaround time for intraoperative pathology reporting may delay clinical decision-making during surgery.

Stimulated Raman Scattering (SRS) microscopy provides the possibility for rapid, label-free, high-resolution microscopic imaging of unprocessed tissue specimens. While SRS has been shown to reveal key diagnostic histologic features in brain tumor specimens, major technical hurdles have hindered its clinical translation. SRS microscopy requires two laser pulse trains that are temporally overlapped by less than the pulse duration (i.e., <100 fs) and spatially overlapped by less than the focal spot size (i.e., <100 nm). Achieving these conditions typically requires free-space optics mounted on optical tables and state-of-the-art, solid-state, continuously water-cooled lasers that are not suitable for use in a clinical environment.

Accordingly, what is desired are systems and methods for intraoperative histopathology that deliver rapid, standardized, and accurate diagnostic images to assist in surgical decision-making. Improved access to intraoperative histologic data enables examination of clinically relevant histologic variations within a tumor and assessment of the resection cavity for residual tumor. In addition, given that the percentage of tumor removed at the time of surgery is a major prognostic factor for brain tumor patients, it would be desirable to develop intraoperative techniques capable of accurately identifying any residual tumor.

This section provides background information related to the present disclosure which is not necessarily prior art.

SUMMARY

This section provides a general summary of the disclosure, and is not a comprehensive disclosure of its full scope or all of its features.

A system is presented for analyzing and interpreting histologic images. In one embodiment, the system is comprised of an imaging device and a diagnostic module. The imaging device captures an image of a tissue sample at an optical section of the tissue sample, where the tissue sample has a thickness larger than the optical section. The diagnostic module is configured to receive the images for the tissue sample from the imaging device and generates a diagnosis for the tissue sample by applying a machine learning algorithm to the images.

In some embodiments, the imaging device generates the images of the tissue sample using Stimulated Raman Scattering. For example, the imaging device images the tissue sample at a first Raman shift in the range from 2820 $cm^{-1}$ to 2880 $cm^{-1}$, and at a second Raman shift in the range from 2920 $cm^{-1}$ to 2980 $cm^{-1}$. The imaging device may further image the tissue sample at a third Raman shift in the range from 2750 $cm^{-1}$ to 2820 $cm^{-1}$.

More specifically, the diagnostic module classifies the tissue sample into categories suing a neural network, such as a convolutional neural network. In one embodiment, the diagnostic module classifies the tissue sample into categories which include a tumoral tissue category or a nontumoral tissue category, where the tumoral tissue category is a tissue sample with a tumor and the nontumoral tissue category is a tissue sample without a tumor. The tumoral tissue category further includes a surgical subcategory and a nonsurgical subcategory, where the surgical subcategory indicates the tumor should be removed by surgery and the nonsurgical subcategory indicates the tumor should not be removed by surgery. The nontumoral tissue category includes a subcategory for normal brain tissue and a subcategory for gliosis tissue. The surgical subcategory includes a subcategory for glial tumors and a subcategory for nonglial tumors. The subcategory for nonglial tumors may further include subcategories for schannoma tumors, meningioma tumors, metastatic tumors, pituitary tumors and medulloblastoma tumors. The subcategory for glial tumors may further include subcategories for glioblastoma tumors and low grade glioma tumors.

In some instances, the diagnostic module classifies the tissue sample into categories which includes a non-diagnostic category for images that cannot be categorized. In this case, the neural network may be trained with images designated as unable to be categorized.

The diagnostic module may also generates a secondary diagnosis for the tissue sample by applying a secondary method to the images and classify the tissue sample in the non-diagnostic category when the secondary diagnosis does not agree with the diagnosis for the tissue sample from the machine learning algorithm, where the secondary method does not use machine learning. In one example, the diagnostic module generates the secondary diagnosis for the tissue sample by determining a quantitative measure of cellularity. In other instances, the diagnostic module generates the primary diagnosis for the tissue sample by determining a quantitative measure of cellularity for the tissue sample.

In some embodiments, the diagnostic module segments a given image of the tissue sample into two or more segments, generates a diagnosis for each segment by applying the machine learning algorithm to the segment, and generates a diagnosis for the tissue sample by aggregating the diagnoses for the segments. For each segment, the diagnostic module can classify the tissue sample into categories using a neural network which thereby yields a probability for each category and normalizes the probabilities across the categories to one. The diagnostic module may generate a diagnosis for the tissue sample by omitting the diagnoses for segments classified in a non-diagnostic category, where the non-diagnostic category indicates that a given segment cannot be categorized. For the given image, the diagnostic module can also set probabilities for any nontumoral tissue categories to zero and renormalizes the probabilities across the categories to one, where the nontumoral tissue categories indicate that a tissue sample is without a tumor.

In another aspect, the system further includes an image interpretation subsystem configured to receive the images from the image device and operates to display the images of the tissue sample. A communication module may be interfaced with the image device and operate to transmit the images from the imaging device to the image interpretation subsystem located remotely from the imaging device.

In some embodiments, the image interpretation subsystem includes a diagnostic module configured to receive the images for the tissue sample and generates a diagnosis for the tissue sample by applying a machine learning algorithm to the images. In these embodiments, the image device may captures images of the tissue sample from at least two different fields of view, and the image interpretation subsystem assembles the images into one assembled image of the tissue sample and displays the assembled image. The diagnostic module also generates a diagnosis for each image received from the imaging device by applying the machine learning algorithm and generates a diagnosis for the tissue sample by aggregating the diagnoses for the images.

In one embodiment, the communication module transmits the images in accordance with the Digital Imaging and Communications in Medicine (DICOM) communication protocol.

In other embodiments, the system includes a picture archiving and communication system (PACS), wherein the communication module communicates the images to PACS for storage.

In yet other embodiments, the image interpretation subsystem transmits an interpretation of the tissue sample from the image interpretation subsystem via a secondary communication link to the imaging device. The interpretation of the tissue sample may be in the form of a DICOM structured report.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 illustrates an exemplary imaging system for obtaining and analyzing optical histologic images according to certain aspects of the present disclosure;

FIG. 2 is a functional block diagram illustrating components of a dual-wavelength fiber-laser-coupled microscope utilized as part of a portable, clinically compatible SRS imaging system. The top arm of the laser diagram indicates the scheme for generating the Stokes beam (red), while the bottom arm generates the pump beam (orange). Both beams are combined (purple) and passed through the specimen according to certain aspects of the present disclosure, where Er=erbium; HLNF=highly nonlinear fiber; PD=photodiode; PPLN=periodically poled lithium niobate; and Yb=ytterbium;

FIG. 4a illustrates an acquired $CH_2$ Raman shift (2,845 $cm^{-1}$) image according to certain aspects of the present disclosure;

FIG. 4b illustrates an acquired $CH_3$ Raman shift (2,930 $cm^{-1}$) image according to certain aspects of the present disclosure;

FIG. 4c illustrates an image reflecting the subtraction operation: $CH_3$ (i.e., image of FIG. 4b) —$CH_2$ (i.e., image of FIG. 4a) according to certain aspects of the present disclosure;

FIG. 4d illustrates assigning the $CH_2$ image to a green channel and assigning the $CH_3$—$CH_2$ image to a blue channel to create a two-color blue-green image according to certain aspects of the present disclosure;

FIG. 4e illustrates an SRH image of a section of a tumor that has been generated by applying a H&E lookup table according to certain aspects of the present disclosure;

FIG. 4f illustrates an image of a similar section of a tumor to that depicted in FIG. 4e that has been generated by performing formalin-fixation, paraffin-embedding (FFPE), and H&E staining according to certain aspects of the present disclosure;

FIG. 5a illustrates a normal cortex that reveals scattered pyramidal neurons (blue arrowheads) with angulated boundaries and lipofuscin granules, which appear red, and white linear structures that are axons (green arrowheads) according to certain aspects of the present disclosure;

FIG. 5b illustrates gliotic tissue that contains reactive astrocytes with radially directed fine protein-rich processes (red arrowheads) and axons (green arrowheads) according to certain aspects of the present disclosure;

FIG. 5c illustrates a macrophage infiltrate near the edge of a glioblastoma that reveals round, swollen cells with lipid-rich phagosomes according to certain aspects of the present disclosure;

FIG. 5d illustrates a SRH that reveals scattered "fried-egg" tumor cells with round nuclei, ample cytoplasm, perinuclear halos (yellow arrowheads), and neuronal satellitosis (purple arrowhead) in a diffuse 1p19q-co-deleted low-grade oligodendroglioma, where Axons (green arrowhead) are apparent in this tumor-infiltrated cortex as well according to certain aspects of the present disclosure;

FIG. 5e illustrates a SRH that demonstrates hypercellularity, anaplasia, and cellular and nuclear pleomorphism in a glioblastoma, including a large binucleated tumor cell is shown (inset) in contrast to smaller adjacent tumor cells according to certain aspects of the present disclosure;

FIG. 5f illustrates a SRH of another glioblastoma reveals microvascular proliferation (orange arrowheads) with protein-rich basement membranes of angiogenic vasculature appearing purple according to certain aspects of the present disclosure;

Figure 6A:
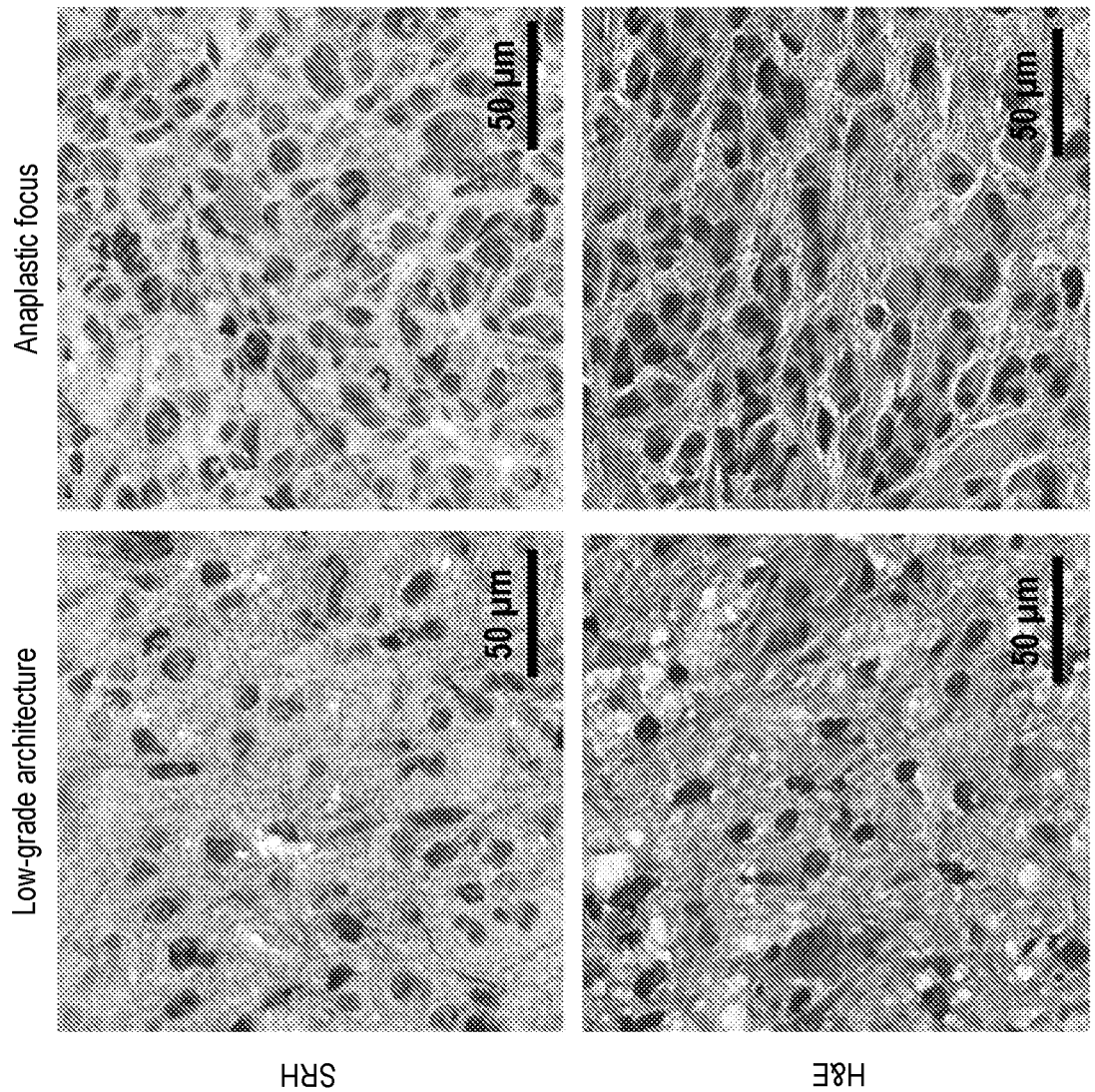
Figure 6A:
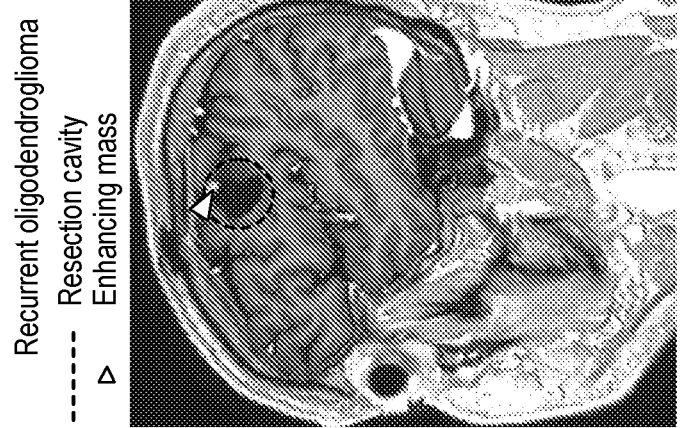
Figure 6B:
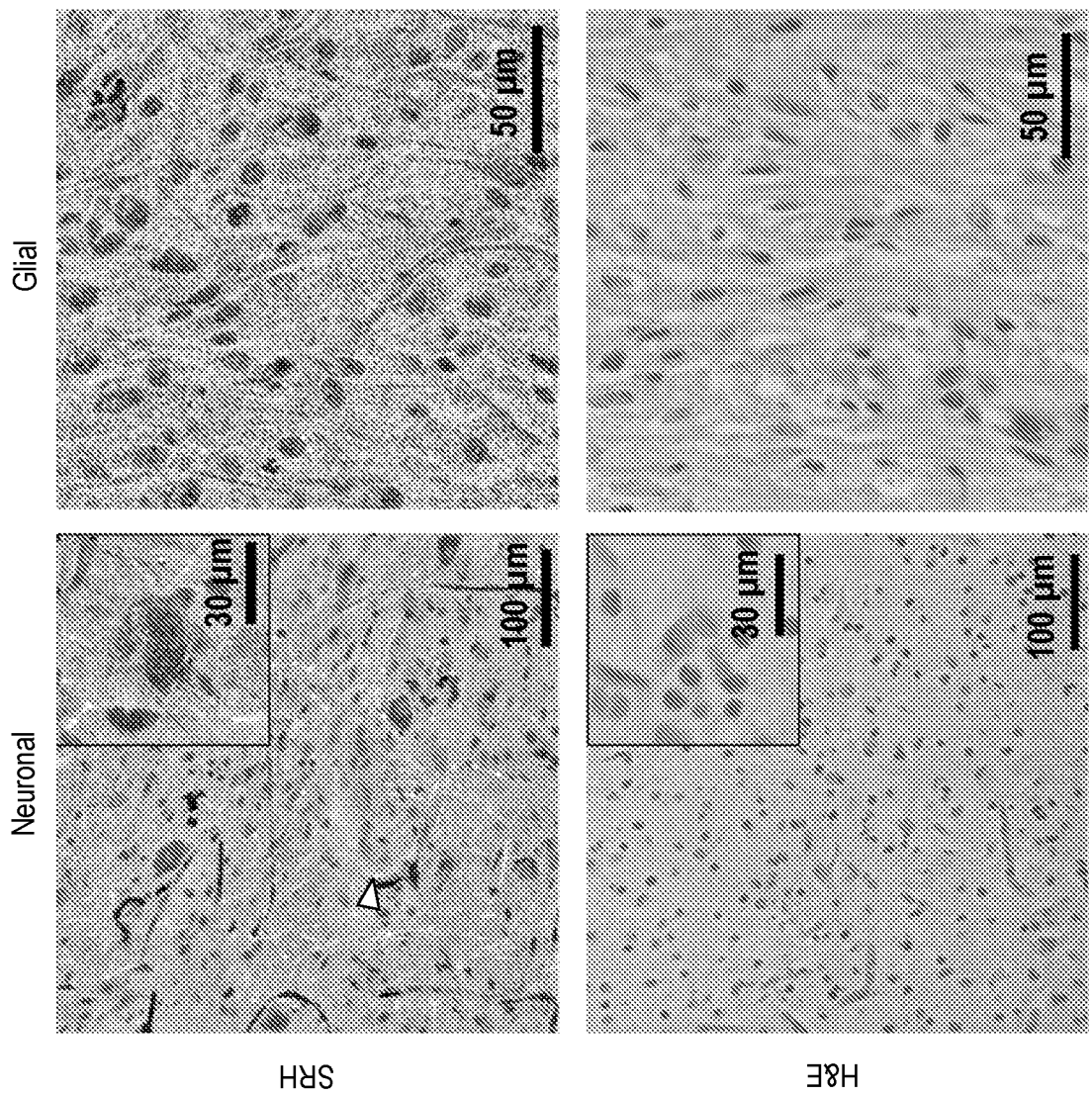
Figure 6B:
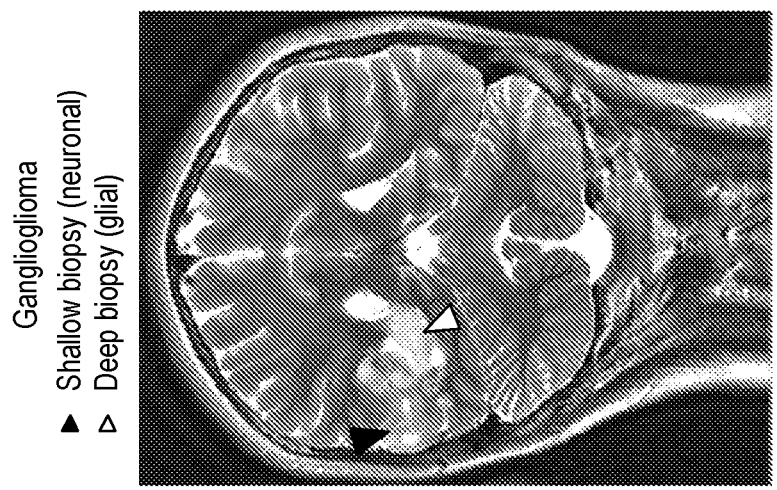
Figure 7A:
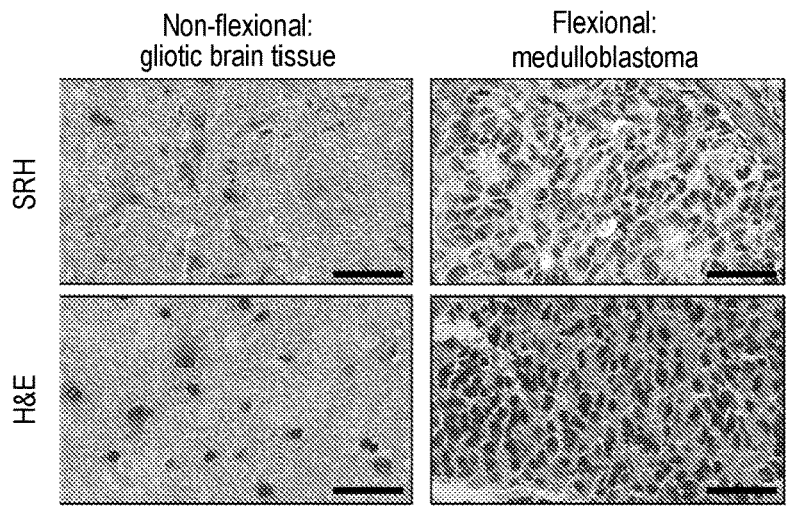
Figure 7B:
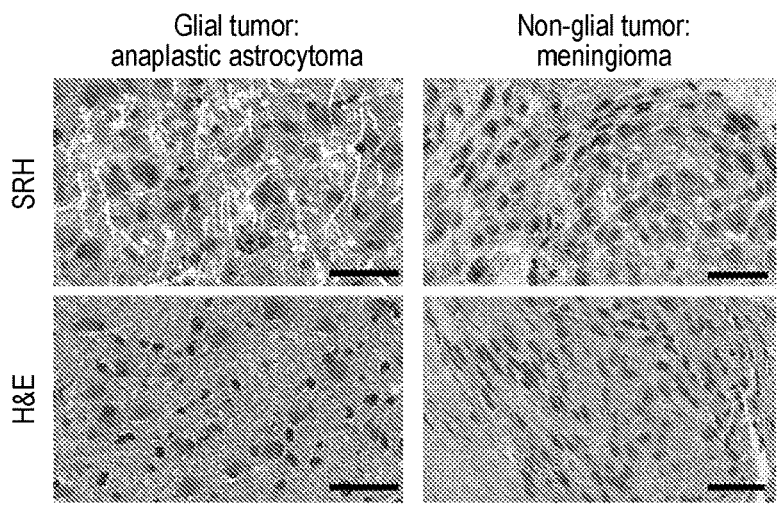
Figure 7C:
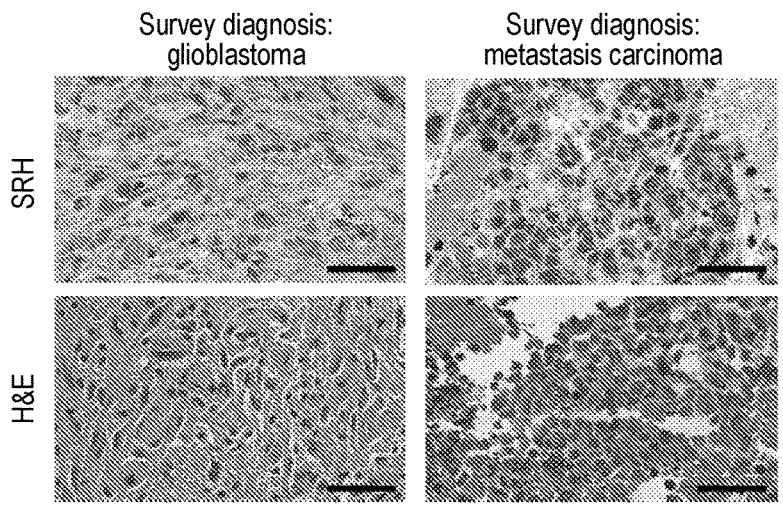
Figure 8A:
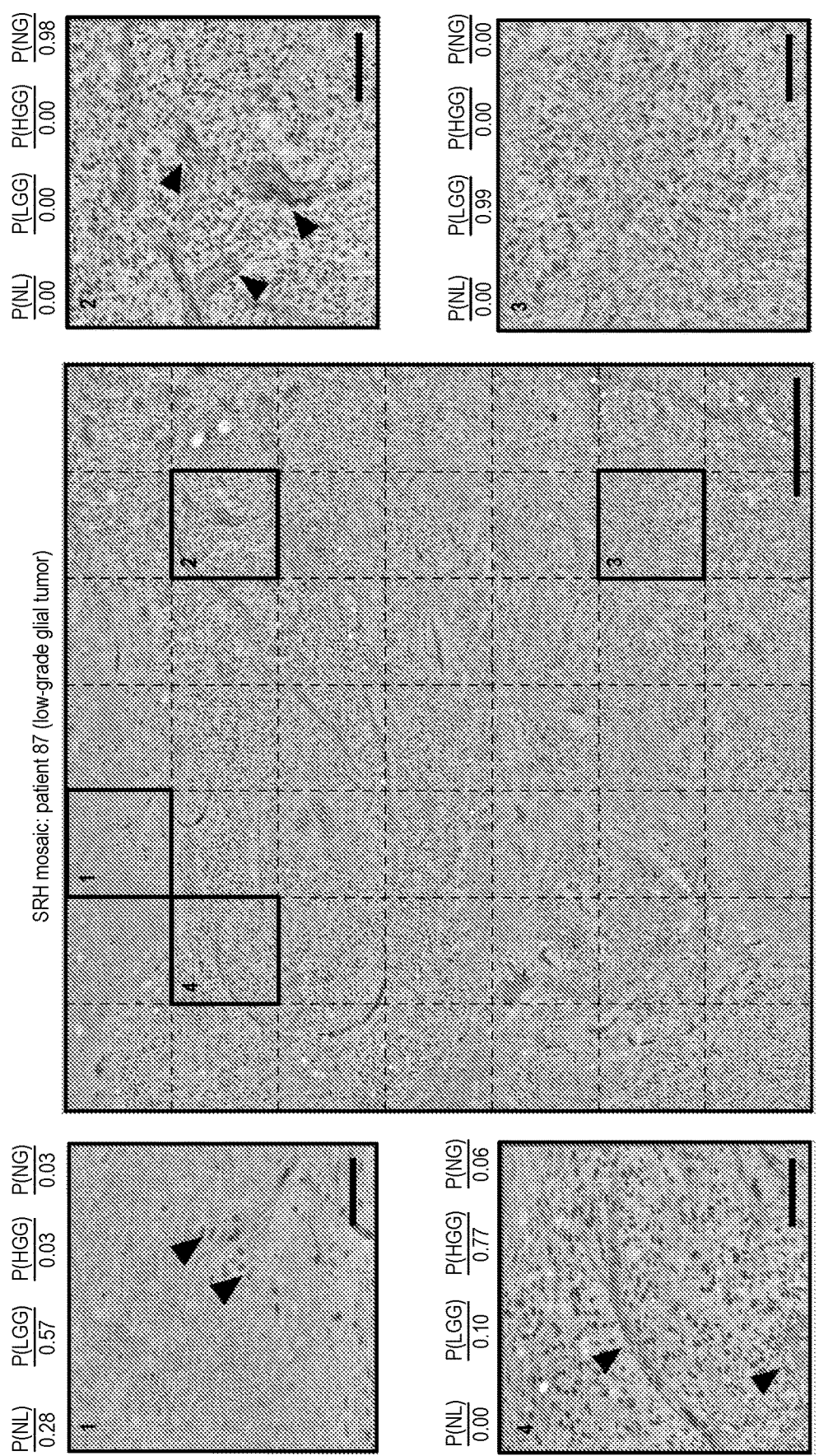
Figure 8B:
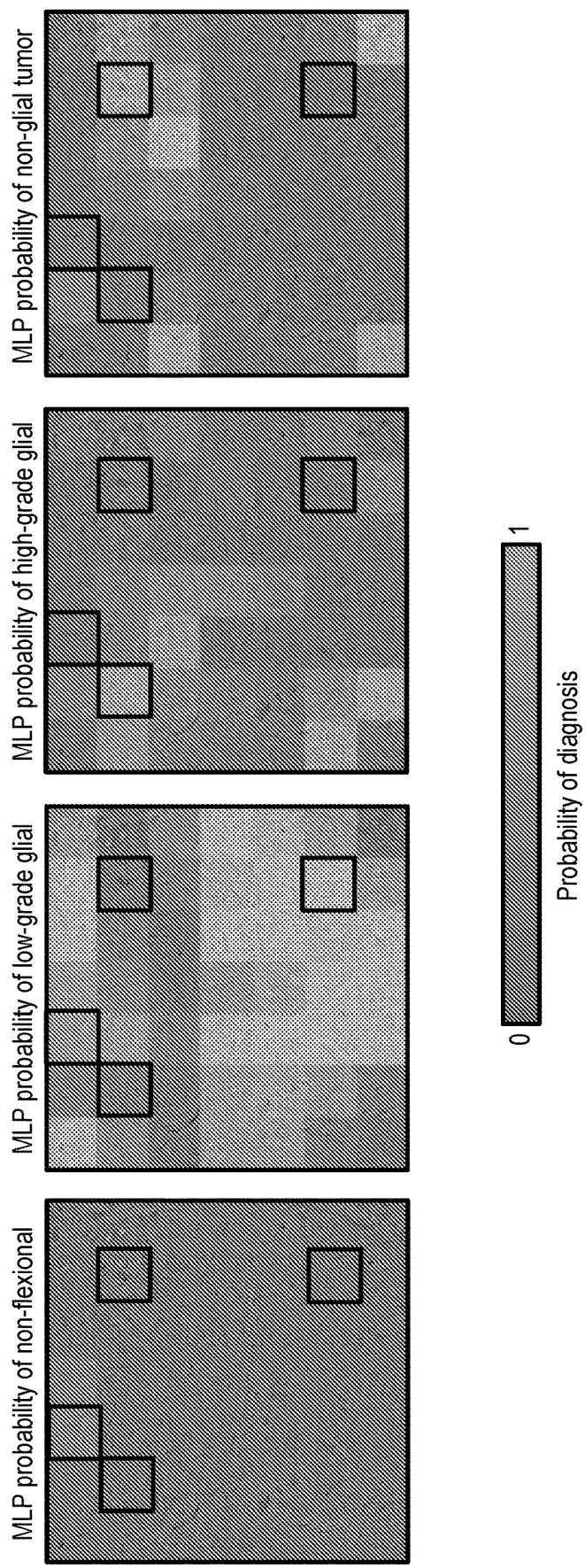
Figure 9C:
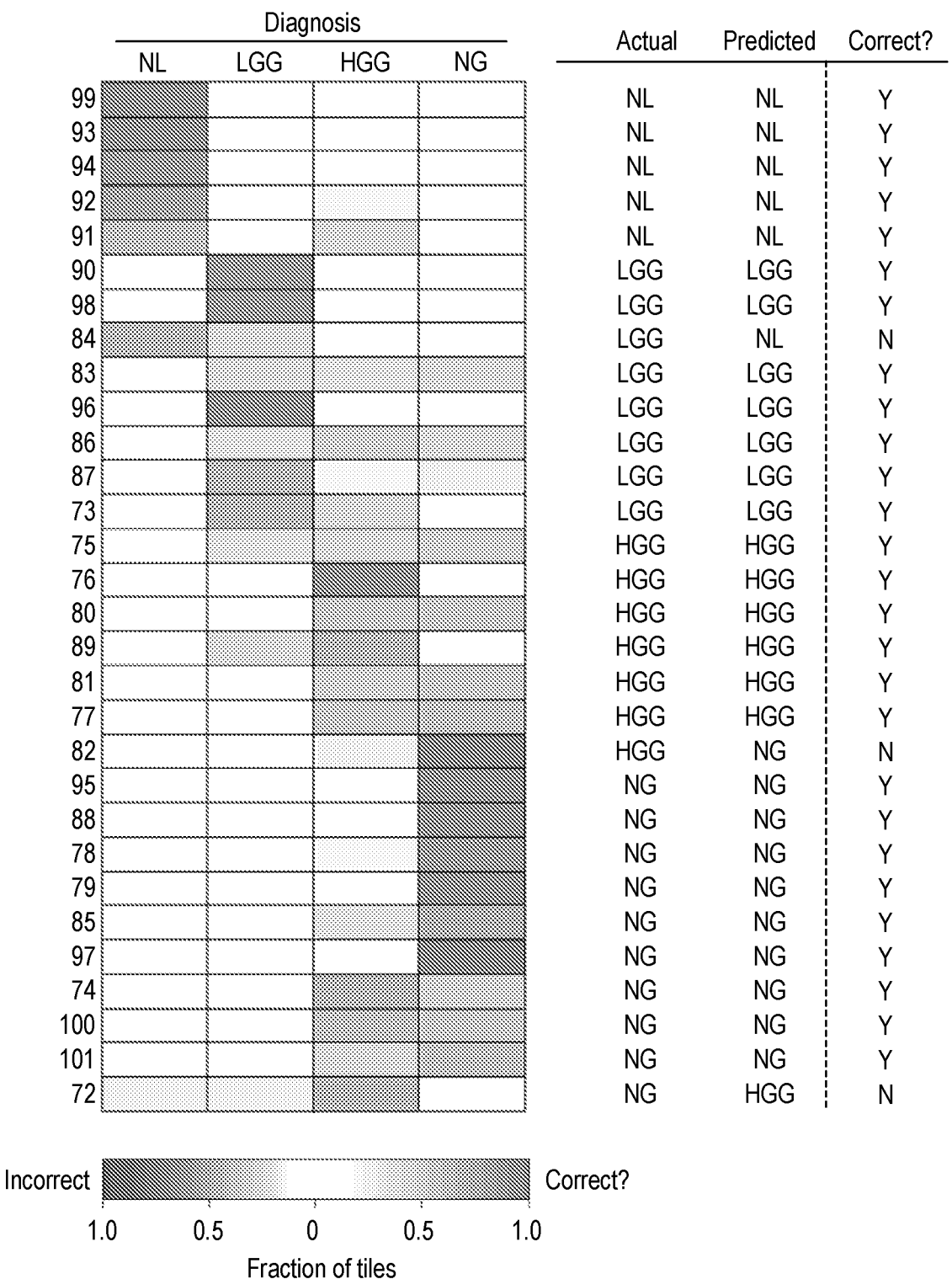
Figure 10:
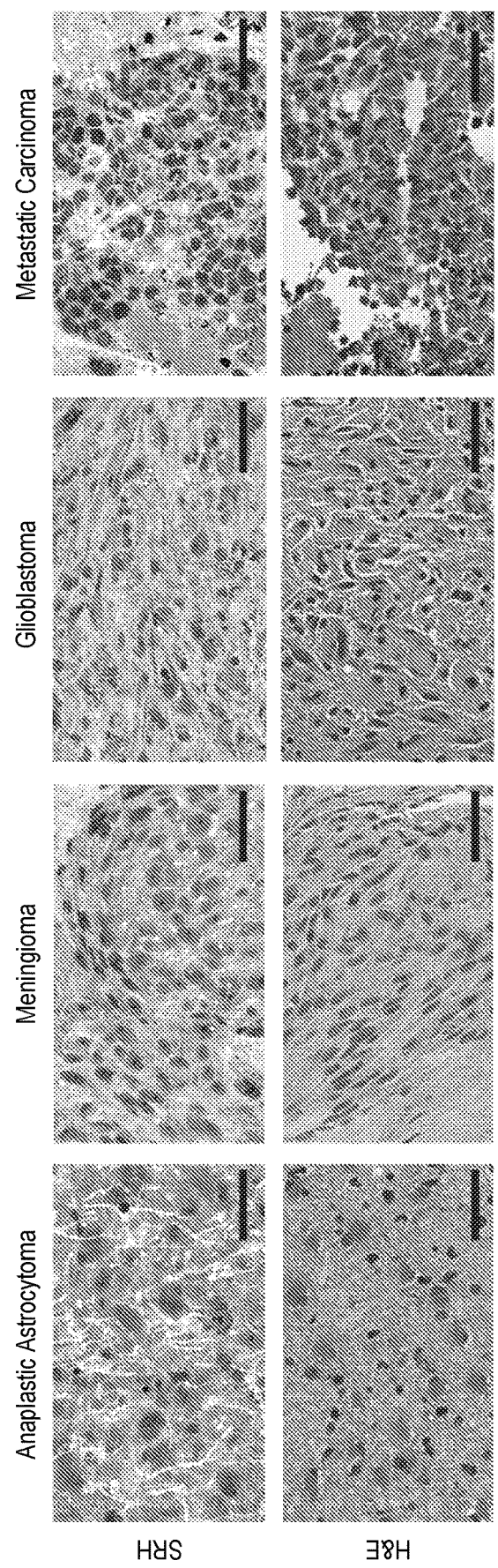
Figure 11:
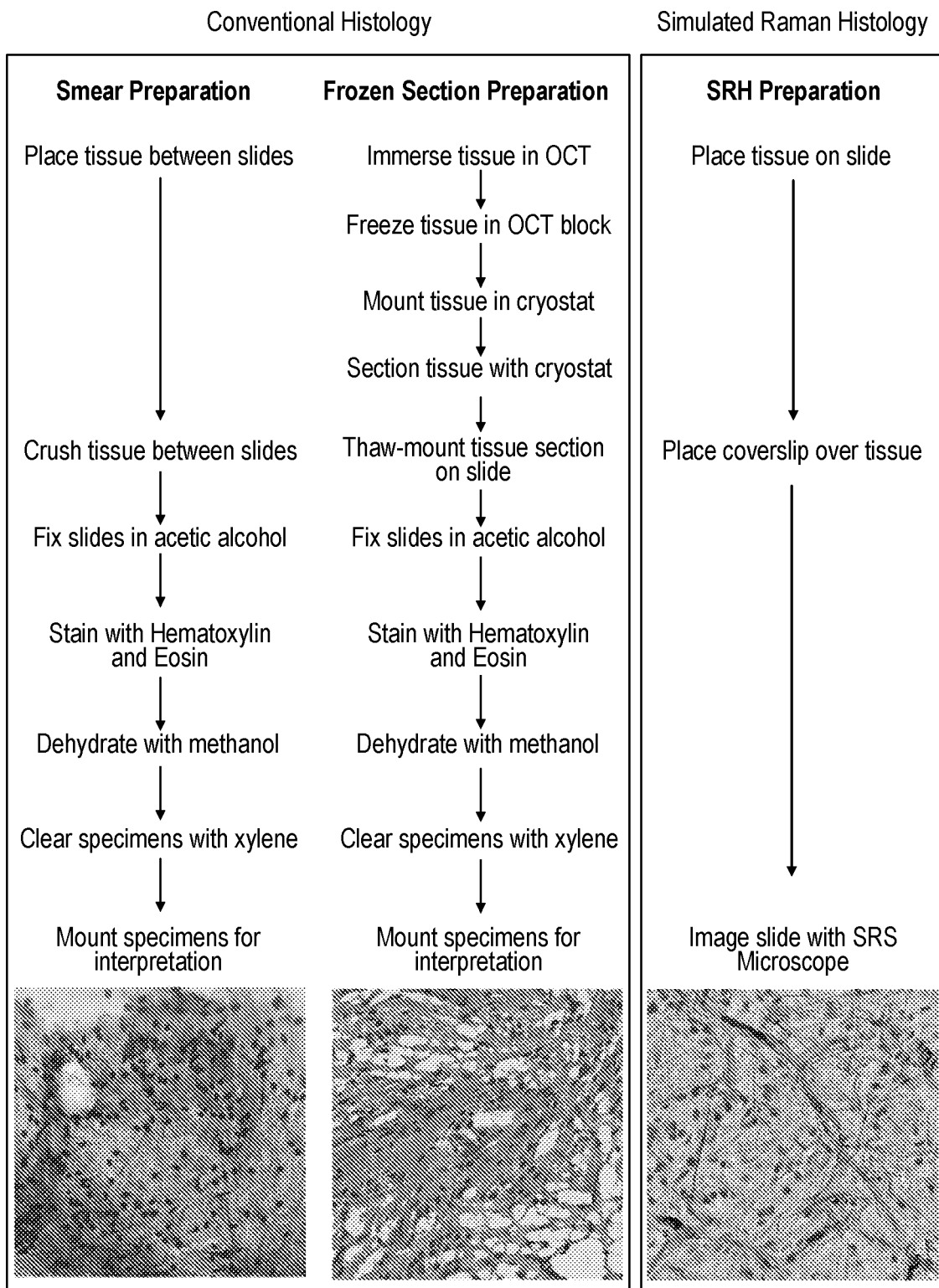
Figure 12:
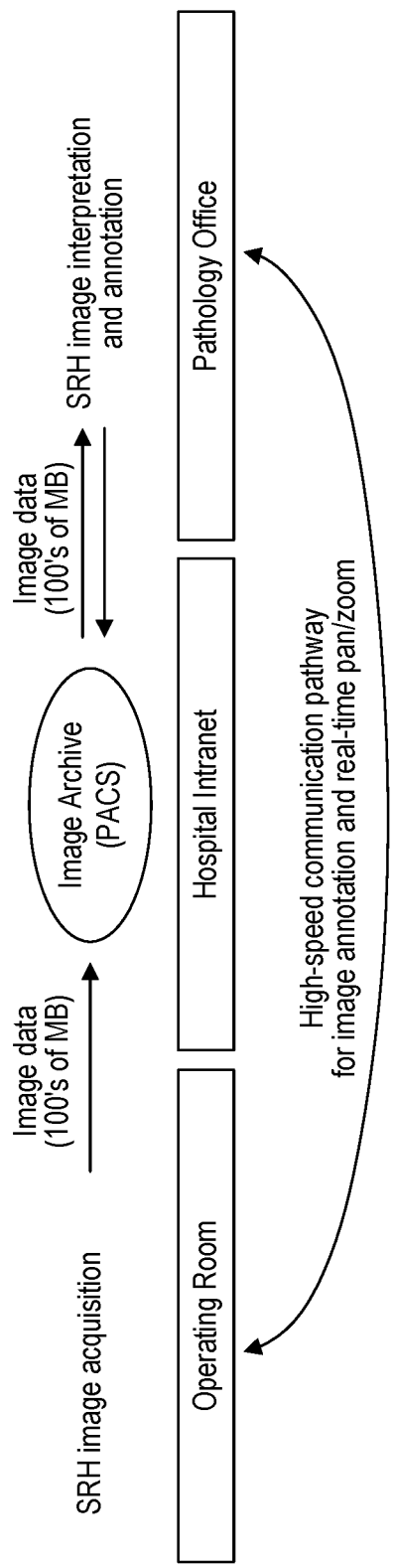
Figure 13:
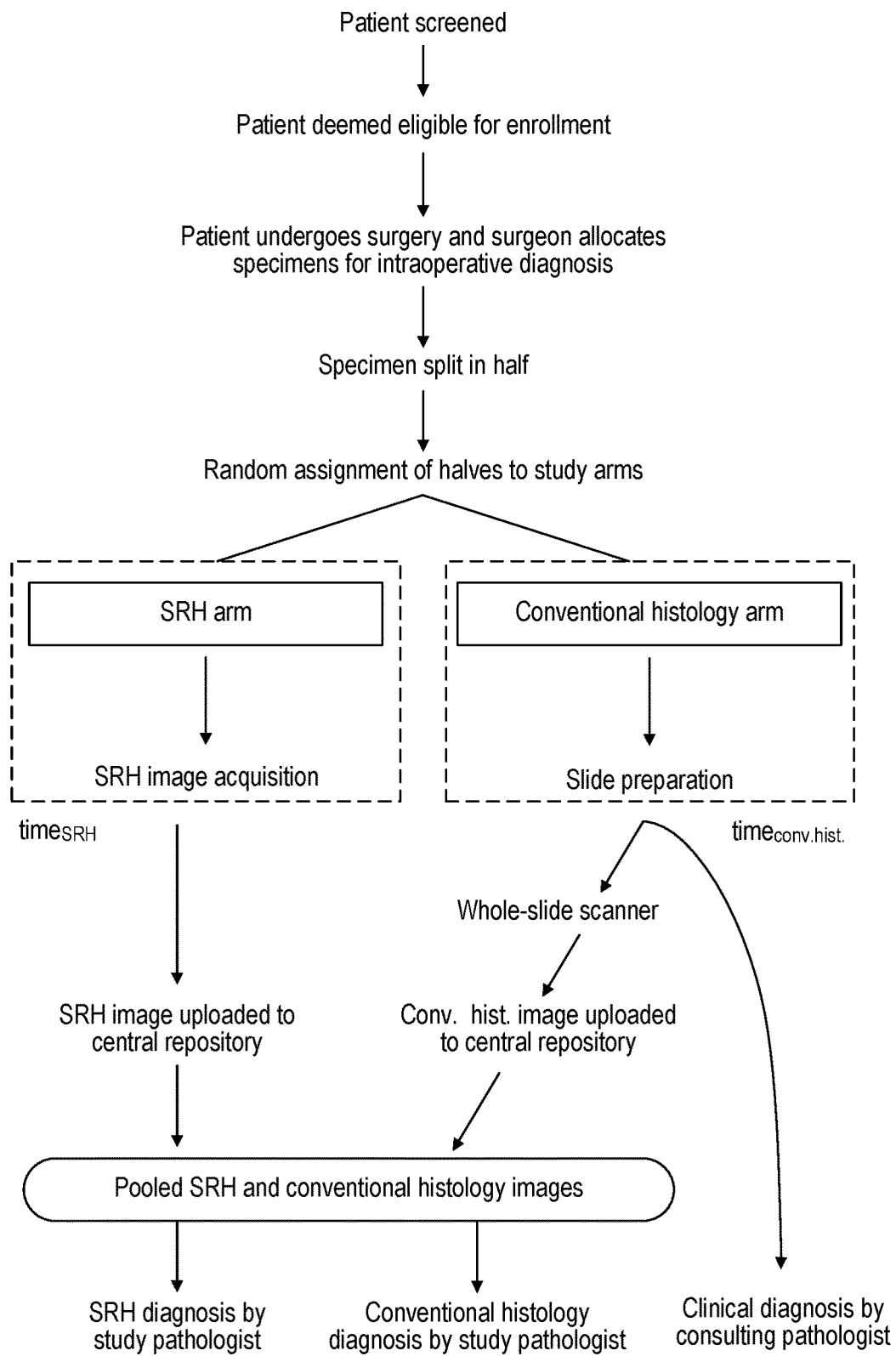
Figure 14:
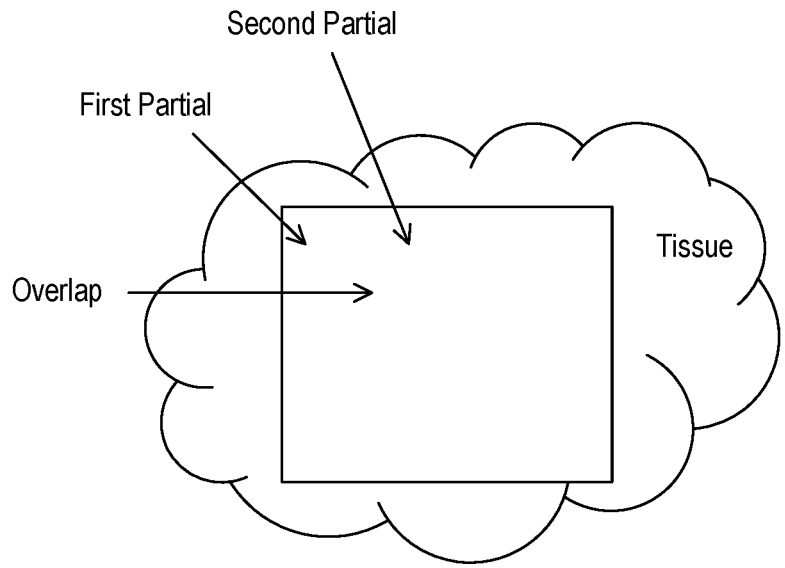
Figure 15:
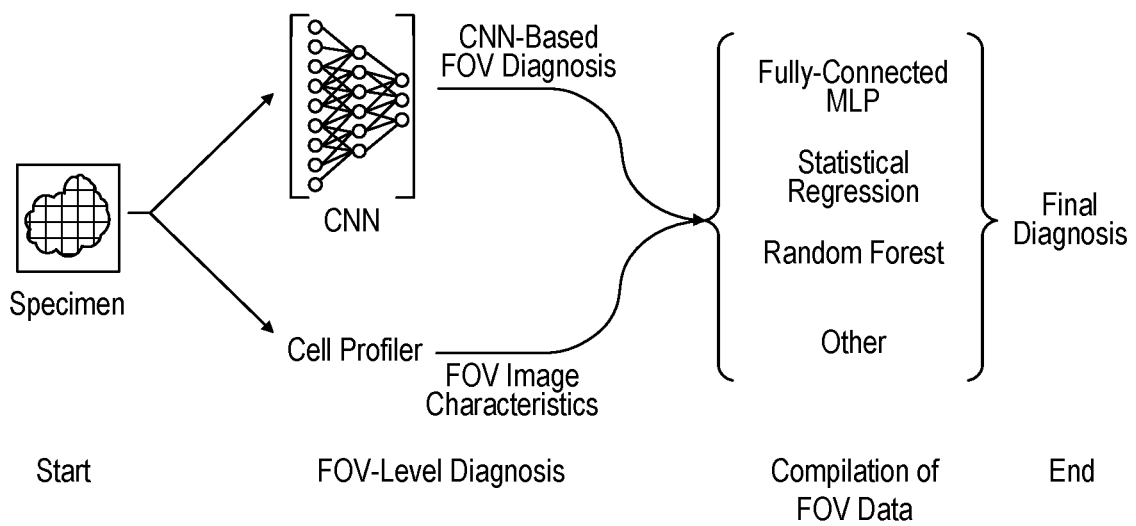

FIG. 6a illustrates (i) on the left-side, a magnetic resonance imaging (MRI) image of a patient with a history of low-grade oligodendroglioma who was followed for an enlarging enhancing mass (yellow arrowhead) in the previous resection cavity (red circle) and (ii) on the right side, SRH imaging of the resected tissue that reveals areas with low-grade oligodendroglioma architecture in some regions (left column) with foci of anaplasia (right column) in other areas of the same specimen according to certain aspects of the present disclosure;

FIG. 6b illustrates (i) on the left-side, a Mill image of a patient with suspected ganglioglioma—gangliogliomas are typically composed of cells of neuronal and glial lineage and (ii) on the right side, SRH imaging that reveals architectural differences between a shallow tissue biopsy at the location indicated with a green arrowhead on the preoperative Mill, where disorganized binucleated dysplastic neurons predominate (left column), and a deeper biopsy (blue arrowhead), where architecture is more consistent with a hypercellular glioma (right column) according to certain aspects of the present disclosure. Formalin-fixation, paraffin-embedding (FFPE), H&E-stained images are shown for comparison;

FIG. 7a illustrates SRH images (top row) and H&E images (bottom row) showing tissue that was judged as non-lesional (left column) or lesional (right column) based on responses from neuropathologists according to certain aspects of the present disclosure;

FIG. 7b illustrates SRH images (top row) and H&E images (bottom row) showing tissue that was judged as glial (left column) or non-glial (right column) based on responses from neuropathologists according to certain aspects of the present disclosure;

FIG. 7c illustrates SRH images (top row) and H&E images (bottom row) showing tissue that was judged as glioblastoma (left column) or metastatic carcinoma (right column) based on responses from neuropathologists according to certain aspects of the present disclosure;

FIG. 8a illustrates a SRH mosaic depicting the low-grade glial tumor diagnostic class with individual FOVs designated by dashed lines (center). Four individual FOVs are depicted at higher scale, with the MLP diagnostic probability for all four categories listed above according to certain aspects of the present disclosure;

FIG. 8b illustrates probability heatmaps overlaid on the SRH mosaic image indicate the MLP-determined probability of class membership for each FOV across the mosaic image for the four diagnostic categories according to certain aspects of the present disclosure. Colored boxes correspond to the FOVs highlighted in FIG. 8a;

Figures 9A, 9B:
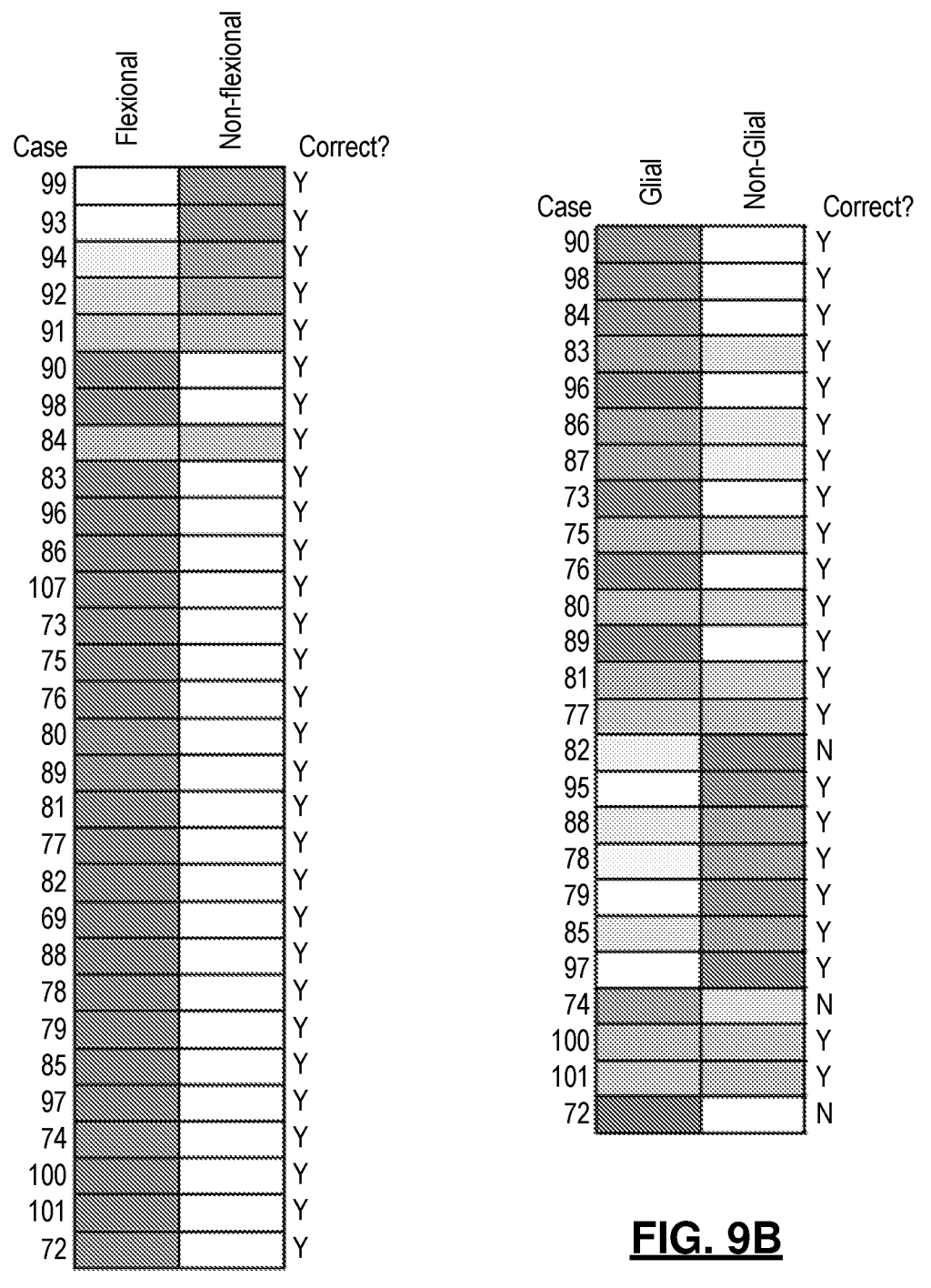

FIG. 9a illustrates a heat map depiction of the classification of cases as lesional or non-lesional via MLP according to certain aspects of the present disclosure. Green checks indicate correct MLP prediction and red circles indicate incorrect prediction;

FIG. 9b illustrates a heat map depiction of the classification of cases as glial or non-glial via MLP according to certain aspects of the present disclosure. Green checks indicate correct MLP prediction, red circles indicate incorrect prediction;

FIG. 9c illustrates a summary of MLP results from a test set of 30 neurosurgical cases (patients 72-101) according to certain aspects of the present disclosure. The fraction of correct tiles is indicated by the hue and intensity of each heat map tile, as well as the predicted diagnostic class;

FIG. 10 illustrates a comparison of label-free, unprocessed SRH images (top row) with conventional H&E stained frozen sections (bottom row) for various cancer types according to certain aspects of the present disclosure;

FIG. 11 illustrates a comparison of conventional histology preparation (left column) with Stimulated Raman Histology (right column) according to certain aspects of the present disclosure;

FIG. 12 illustrates a network architecture enabling bidirectional transfer and annotation of SRH images according to certain aspects of the present disclosure;

FIG. 13 is a flowchart illustrating a method for performing diagnosis using pooled SRH and conventional histology images according to certain aspects of the present disclosure;

FIG. 14 is a diagram illustrating stitched image acquisition according to certain aspects of the present disclosure; and FIG. 15 is a flowchart illustrating a method for performing a diagnosis using a convolutional neural network (CNN) according to certain aspects of the present disclosure.

Figure 16:
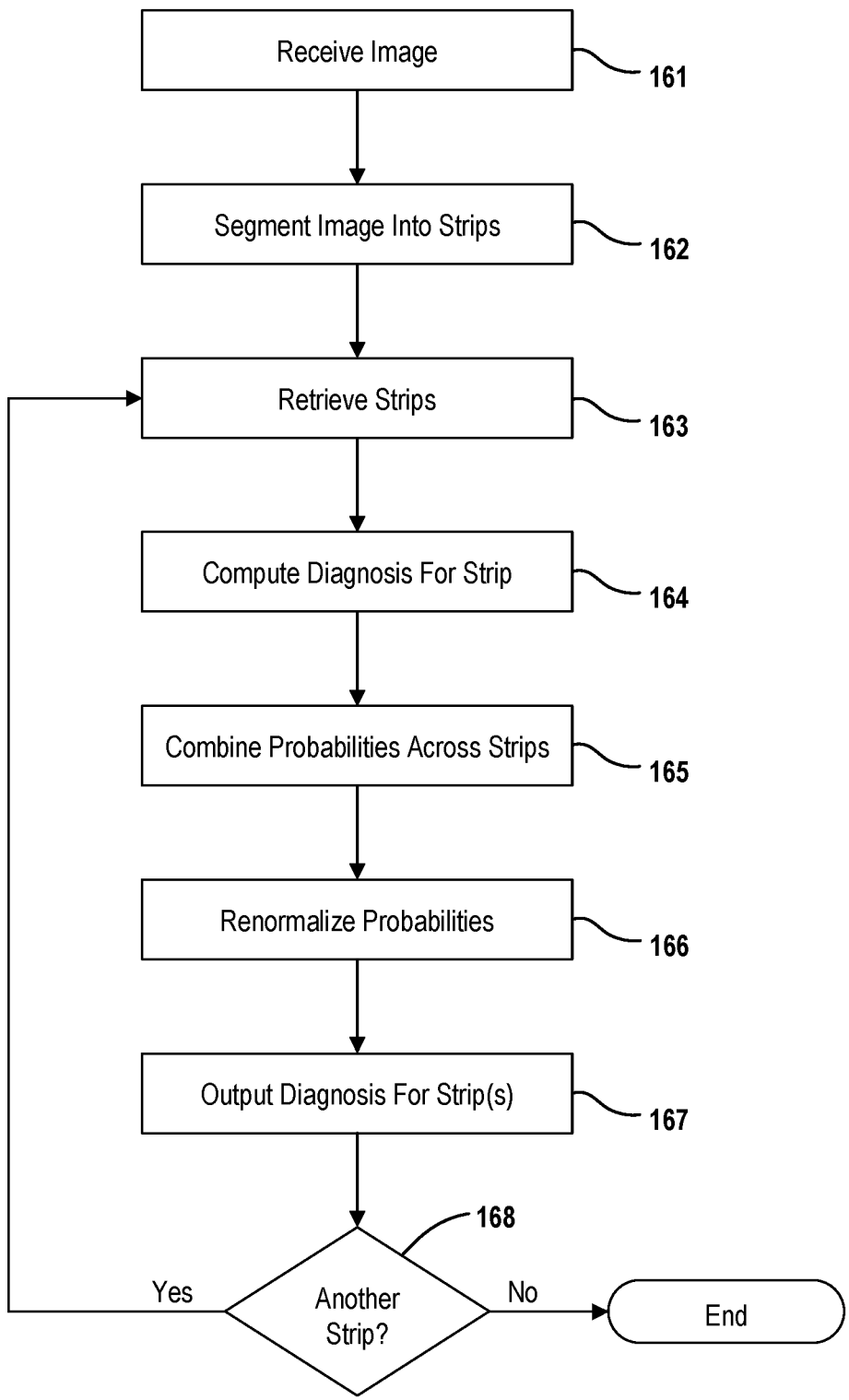
Figure 17:
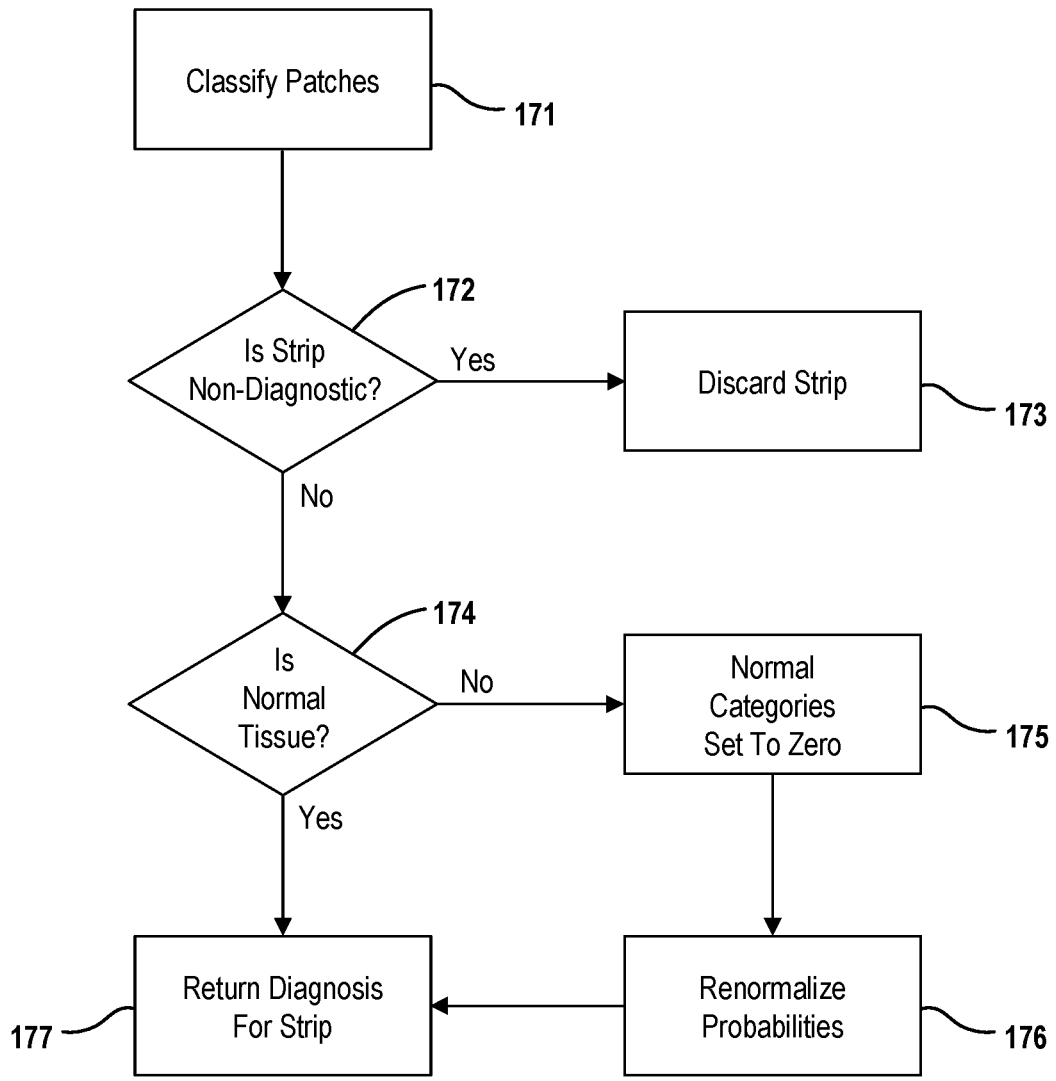
Figure 18:
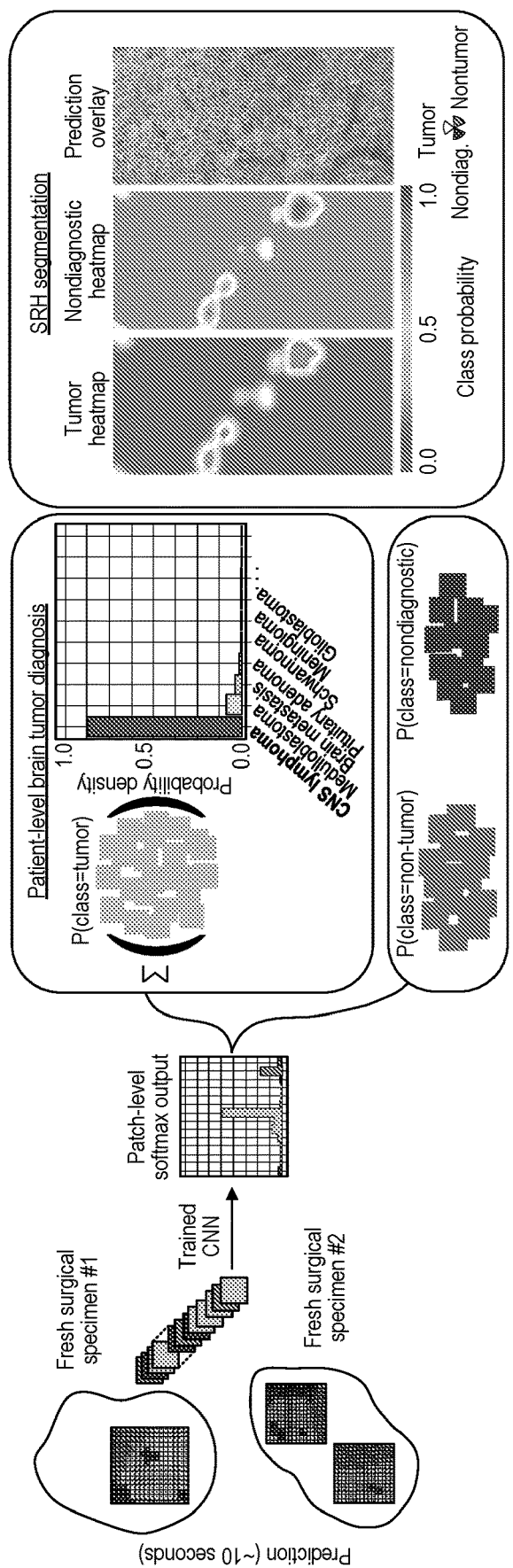
Figure 19:
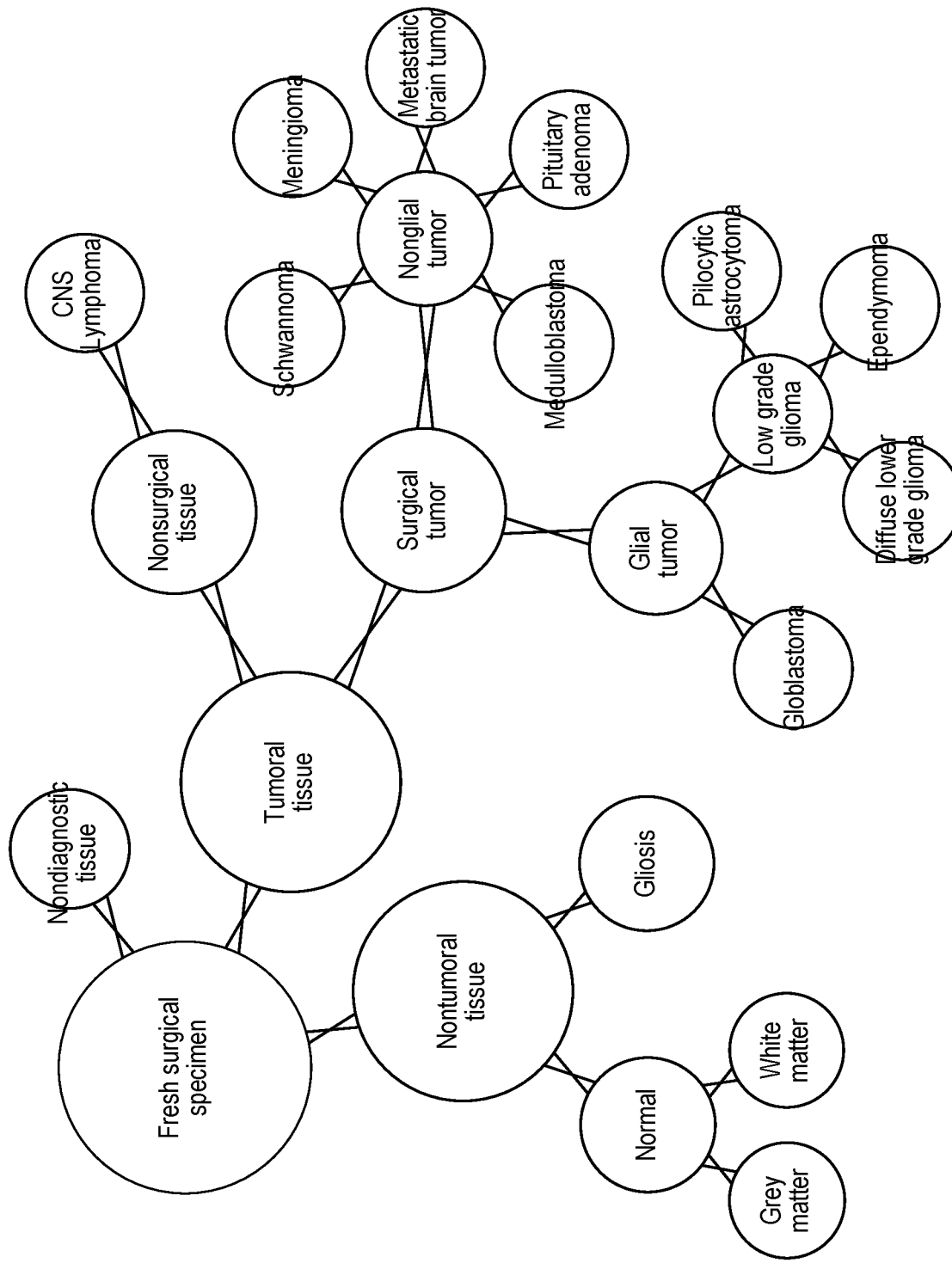

FIG. 16 is a flowchart depicting an example method for analyzing SRH images;

FIG. 17 is a flowchart depicting an example method for determining a diagnosis fora strip;

FIG. 18 is a diagram further illustrating the example method for analyzing SRH images; and FIG. 19 is a diagram depicting an example set of categories for the classification model.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

Leveraging advances in fiber-laser technology, the instant disclosure presents a clinical SRS microscope, allowing for the execution of SRS microscopy in a patient care setting. Light guiding by an optical core of the fiber and the unique polarization-maintaining (PM) implementation of the laser source enables service-free operation in operating rooms. The systems described herein also include improved noise cancellation electronics for the suppression of high relative intensity noise, one of the major challenges of executing fiber-laser-based SRS microscopy.

The system described herein demonstrates, among other things, that SRS microscopy can serve as an effective, streamlined alternative to traditional histologic methods, eliminating the need to transfer specimens out of the operating room to a pathology laboratory for sectioning, mounting, dyeing, and interpretation. Moreover, because tissue preparation for SRS microscopy is minimal, key tissue architectural details commonly lost in smear preparations and cytologic features often obscured in frozen sections are preserved. In addition, the instant disclosure presents a method for SRS image processing that simulates hematoxylin and eosin (H&E) staining, called Stimulated Raman Histology (SRH), which highlights key histoarchitectural features of tumors (e.g., brain tumors) and enables diagnosis in substantial agreement with conventional H&E-based techniques. Furthermore, the instant disclosure describes how various supervised machine learning approaches based, for example, on quantified SRH image attributes, effectively differentiate among diagnostic classes of brain tumors. Thus, SRH may provide an automated, standardized method for intraoperative histopathology that can be leveraged to improve the surgical care of brain tumors in the future.

Aspects of the present disclosure describe the use of SRS images in tissue diagnosis. However, the concepts and implementations described herein are equally applicable to other fresh-tissue imaging modalities that produce an optical section of a thick tissue specimen. These may include label-free imaging technologies such as, but not limited to, confocal reflection microscopy, one- or two-photon autofluorescence microscopy, fluorescent lifetime imaging (FLIM), second-harmonic generation (SHG) microscopy, third-harmonic generation (THG) microscopy, and or coherent anti-stokes Raman scattering (CARS) microscopy. In addition, the systems and methods described herein may also utilize label- or stain-based imaging technologies, such as one- or two-photon fluorescence confocal or wide-field microscopy or light sheet microscopy. Typical intra-vital stains include, but are not limited to, DAPI, eosin, rhodamine, Hoechst stains or acridine orange. In some examples, the systems and methods described herein may utilize a combination of label-free and label- or stain-based imaging technologies.

The common feature between all these techniques is optical sectioning. This stands in contrast to physical sectioning of the tissue specimen as typically done in routing histopathology. It means that the image is generated from a focal plane inside the tissue specimen that has a thickness smaller than the specimen itself. Out-of-focus signal is either not generated or rejected. The thickness of the optical section can be determined by the numerical aperture of the objective lens used. Using these technologies, it is possible but not required to acquire a depth stack of a specimen at various depths from the sample surface. In one example, this can be achieved by systematically varying the distance between the sample and the objective lens.

Figure 1:
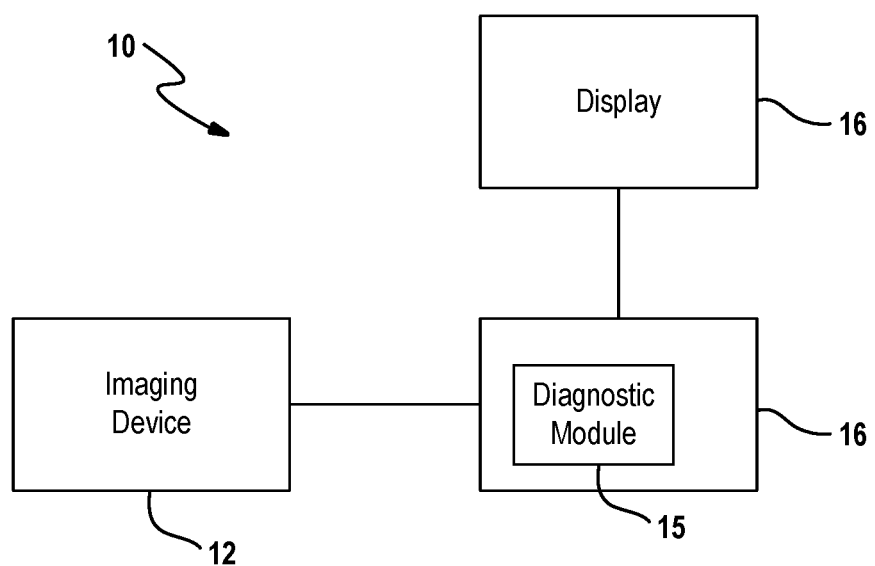

Referring now to FIG. 1, an exemplary imaging system 10 for obtaining and analyzing optical histologic images is shown. The imaging system 10 is comprised generally of an imaging device 12 and a diagnostic module 15 implemented on a computing device 14. During operation, the imaging device captures one or more images of a fresh tissue sample using optical sectioning. That is, the imaging device 12 captures an images of the tissue sample at an optical section of the tissue sample, where the tissue sample has a thickness larger than the optical section. In the example embodiment, the imaging device 12 generates images of a tissue sample using Stimulated Raman Scattering. The diagnostic modules 15 is configured to receive the images from the imaging device 12 and generate a diagnosis for the tissue sample by applying a machine learning algorithm to the images as further described below. The imaging system 10 may also include a display device 16 for displaying diagnostic results.

More specifically, the fully-integrated Stimulated Raman Scattering (SRS) imaging system 10 includes five major components: 1) a fiber-coupled Stimulated Raman Scattering (SRS) microscope with a motorized stage; 2) a dual-wavelength fiber-laser module; 3) a laser control module; 4) a microscope control module; and 5) a computer for image acquisition, display, and processing. The entire system may be mounted in a portable, self-contained clinical cart, may utilize a standard wall plug, and may avoid the use of water-cooling. In this manner, the system of FIG. 1 may eliminate reliance on optical hardware incompatible with the execution of SRS microscopy in an operating room.

Figure 2:
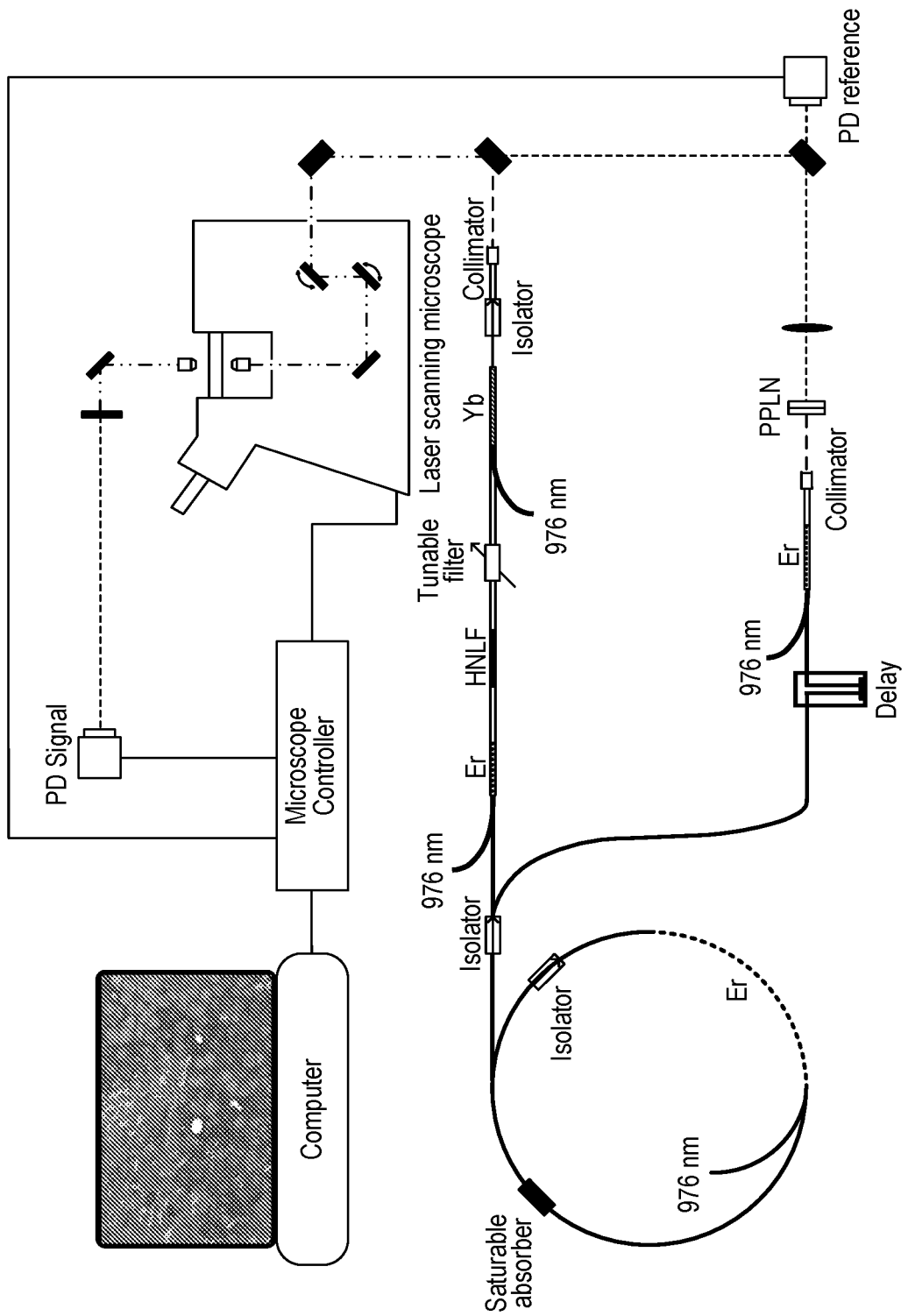

FIG. 2 is a functional block diagram further illustrating one example of the imaging system 10. FIG. 2 illustrates components of a dual-wavelength fiber-laser-coupled microscope utilized as part of a portable, clinically compatible SRS imaging system (e.g., the SRS imaging system of FIG. 1). In FIG. 2, the top arm of the laser diagram indicates the scheme for generating the Stokes beam (red), while the bottom arm generates the pump beam (orange). Both beams are combined (purple) and passed through the specimen, where Er=erbium; HLNF=highly nonlinear fiber; PD=photodiode; PPLN=periodically poled lithium niobate; and Yb=ytterbium;

The dual-wavelength fiber-laser may operate based on the fact that the difference frequency of the two major fiber gain media, Erbium (Er) and Ytterbium (Yb), overlaps with the high wavenumber region of Raman spectra. Accordingly, the two synchronized narrow-band laser pulse-trains required for SRS imaging are generated by narrow-band filtering of a broad-band super-continuum derived from a single fiber-oscillator and, subsequently, amplification in the respective gain media, as shown, for example, with respect to FIG. 2.

According to some examples, (e.g., for clinical implementation), the imaging systems of FIGS. 1-2 may constitute all-fiber systems based on polarization-maintaining (PM) components, which may offer significant improvements in stability over non-PM systems. The systems described with regard to FIGS. 1-2 herein may maintain stability throughout transcontinental shipping (e.g., from California to Michigan), and continuous, service-free, long-term (>1 year) operation in a clinical environment, without the need for realignment. To enable high-speed diagnostic-quality imaging (e.g., 1 megapixel in 2 seconds per wavelength) with a signal-to-noise ratio comparable to what can be achieved with solid-state lasers, the laser output power may be scaled to approximately 120 mW for the fixed wavelength 790 nm pump beam and approximately 150 mW for the tunable Stokes beam over the entire tuning range from 1010 nm to 1040 nm at 40 MHz repetition rate and 2 picosecond transform-limited pulse duration. According to some examples, fully custom laser controller electronics may be included as part of the imaging system to tightly control the many settings of this multi-stage laser system based on a micro-controller. Once assembled, the SRS microscope may include, according to some examples, a lateral resolution of 360 nm (full width of half maximum) and axial resolution of 1.8 μm.

Figure 3A:
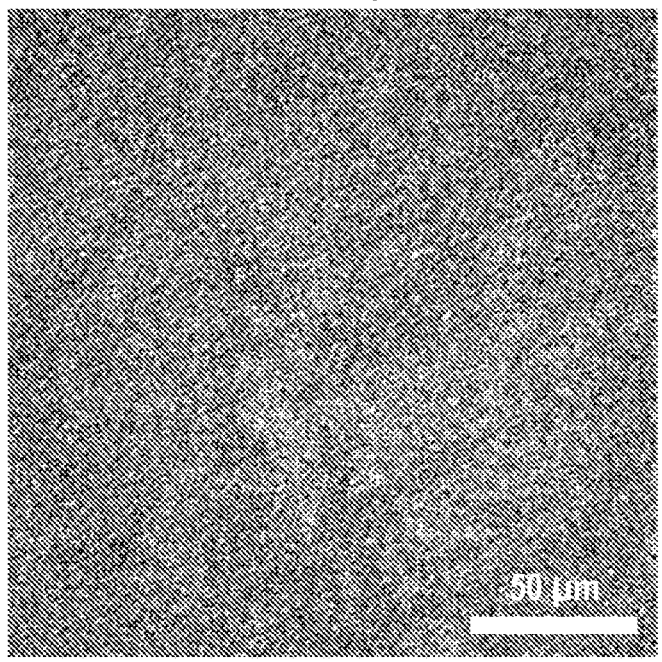
FIG. 3a illustrates a raw 2845 $cm^{-1}$ SRS image of human tissue before noise cancellation according to certain aspects of the present disclosure.
Figure 3B:
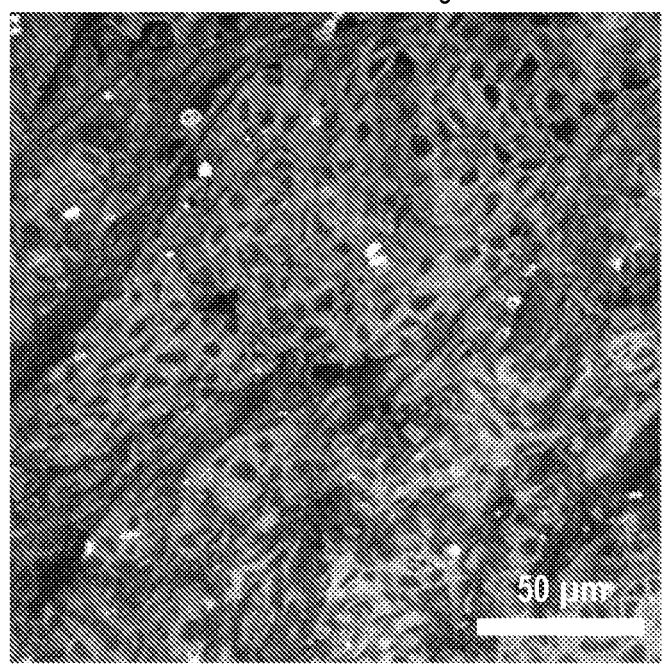
FIG. 3b illustrates a raw 2845 $cm^{-1}$ SRS image of human tissue after balanced-detection-based noise cancellation according to certain aspects of the present disclosure.

While development of an all-fiber system may be desired for clinical implementation of SRS, relative intensity noise intrinsic to fiber lasers may vastly degrade SRS image quality, as shown in FIG. 3a. To improve image quality, the imaging system described herein may implement a noise-cancelation scheme based on auto-balanced detection, in which a portion of the laser beam is sampled to provide a measure of the laser noise that can then be subtracted in real-time. According to some examples, ~25× improvement may be achieved in the signal-to-noise ratio in a clinical setting, without the need for adjustment, which is essential for revealing microscopic tissue architecture, as shown in FIG. 3b.

FIGS. 4a-4e illustrate an exemplary method for processing SRS images into SRH images according to certain aspects of the present disclosure. That is, FIGS. 4a-4d illustrate a method for converting one or more SRS images into a SRH image—such as the SRH image shown in FIG. 4e—such that the SRH image shown in FIG. 4e closely resembles an image (see FIG. 4f) produced according to conventional formalin-fixation, paraffin-embedding and acidic (hematoxylin) or basic (eosin) (H&E) staining.

By way of background, Raman spectra of common molecules, such as lipids, proteins, and nucleic acids like DNA in tissue can be imaged in tissue at multiple Raman shifts (such as, for example, at 2850 cm$^{-1}$ and 2930 cm$^{-1}$ or 2850 cm$^{-1}$, 2930 cm$^{-1}$ and 2960 cm$^{-1}$). Using spectral unmixing techniques, multicolor SRS images can be generated that can be displayed in different pseudo colors, such as, for example, blue and green in or a pink and purple to mimic H&E staining, by way of example. SRS images of the $CH_2$-vibration (2845 cm$^{-1}$) show lipid-rich structures, such as myelinated axons and extracellular matrix. SRS images of the $CH_3$-vibration (2930 cm$^{-1}$) show protein- and DNA-rich structures such as nuclei and collagen fibers. Such SRS images can be overlaid or stitched together. The unique chemical contrast specific to SRS microscopy enables tumor detection by revealing quantifiable alterations in tissue cellularity, axonal density and protein:lipid ratio in tumor-infiltrated tissues, for example.

Figure 4G:
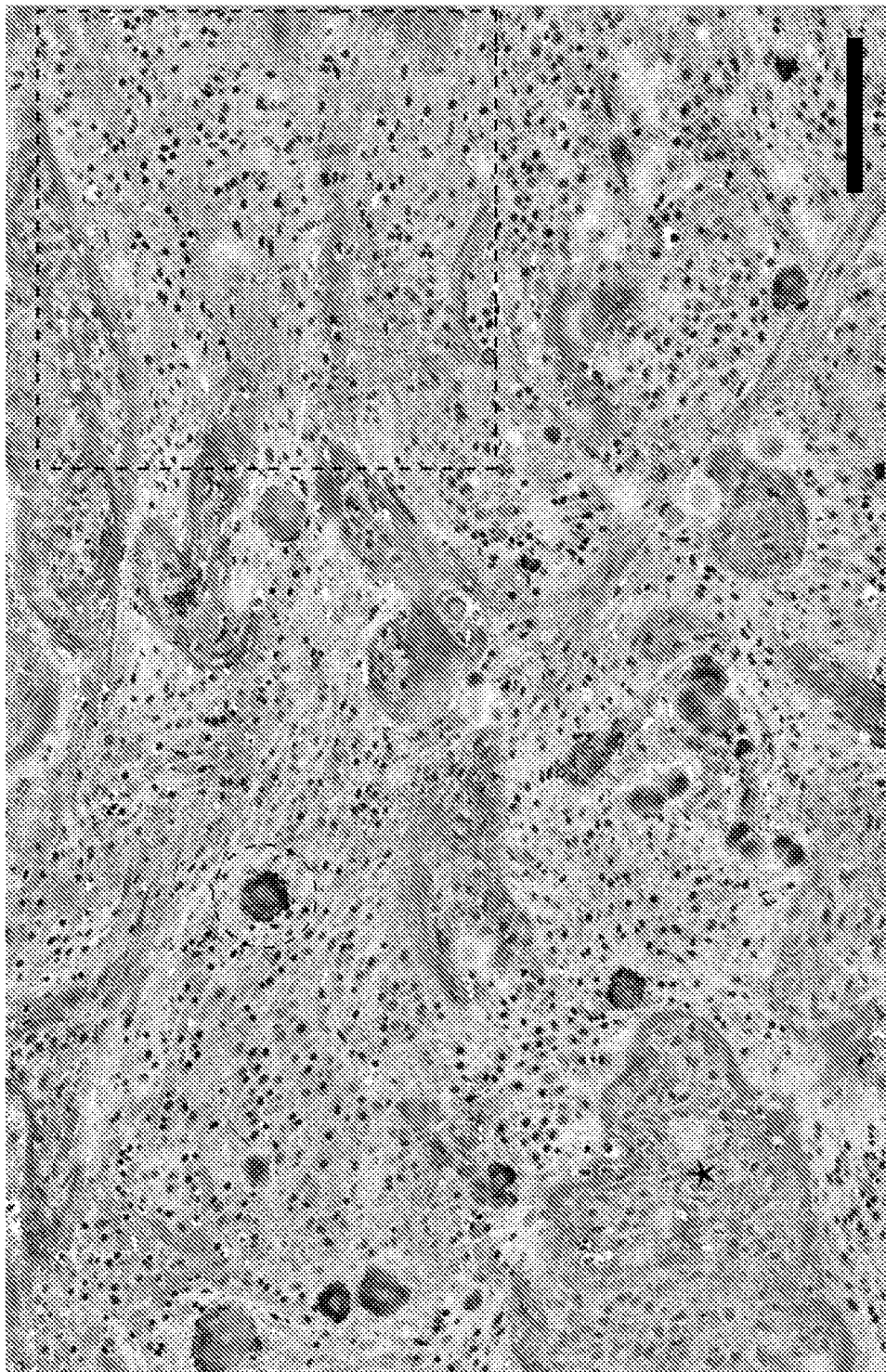
FIG. 4g illustrates a mosaic tiled image of several SRH filed of views (FOVs) to create a mosaic of imaged tissue. The star indicates a focus of microvascular proliferation, the dashed circle indicates calcification, and the dashed box demonstrates how the FOV in FIG. 4e fits into the larger mosaic according to certain aspects of the present disclosure (scale bars=100 μm)

A classification scheme might integrate robust, quantified SRS image attributes (e.g., hypercellularity, axonal density, protein:lipid ratio) into a single metric for detecting infiltration. Thus, in certain aspects, the number of nuclei, axonal density and protein:lipid ratio can be assessed from an SRS image. Unlike previous methods for achieving virtual H&E images through hyperspectral SRS microscopy, SRH is capable of employing only two Raman shifts (e.g., 2845 cm$^{-1}$ and 2930 cm$^{-1}$) to generate the necessary contrast. Though the colors in SRH images do not correspond exactly with the staining of acidic (hematoxylin) or basic (eosin) moieties, there is strong overlap between the two methods (see FIG. 4f), simplifying interpretation. To produce SRH images, fields-of-view (FOVs) may be acquired at a speed of 2 seconds per frame in a mosaic pattern, stitched, and recolored. The end result may be a SRH mosaic (as shown in FIG. 4g) resembling a traditional H&E-stained slide. According to one example, the time of acquisition for the mosaic may be about 2.5 min, and it can be rapidly transmitted to any networked workstation directly from an operating room, as described in additional detail below.

Figure 5I:
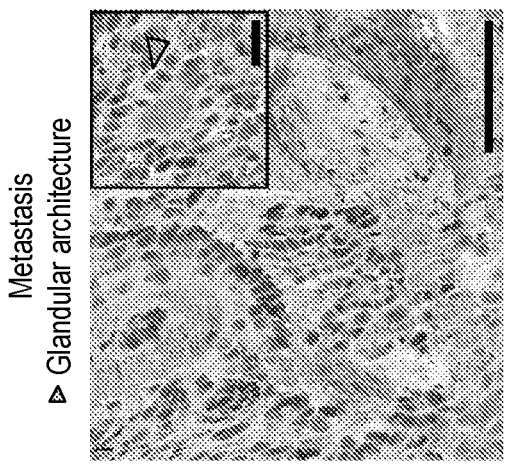
FIG. 5i illustrates a SRH that reveals the glandular architecture (inset; gray arrowhead) of a metastatic colorectal adenocarcinoma according to certain aspects of the present disclosure (large image scale bars=100 μm; inset image scale bars=20 μm)

According to some examples of the present disclosure, SRH may be employed in the detection of diagnostic histologic features with SRH. SRH has demonstrated an ability to reveal the diagnostic features required to detect and classify tumors of the CNS by imaging fresh surgical specimens from neurosurgical patients via an institutional review board (IRB)-approved protocol. Like conventional H&E images, SRH images reveal the cellular and architectural features that permit differentiation of non-lesional (as shown in FIGS. 5a-5c) and lesional (as shown in FIGS. 5d-5i) tissues. When imaged with SRH, architecturally normal brain tissue from anterior temporal lobectomy patients demonstrates neurons with angular cell bodies containing lipofuscin granules (as shown in FIG. 5a), and lipid-rich axons that appear as white linear structures (as shown in FIGS. 5a-5b). Non-neoplastic reactive changes including gliosis (as shown in FIG. 5b) and macrophage infiltration (as shown in FIG. 5c) that may complicate intraoperative diagnosis are also readily visualized with SRH. Differences in cellularity, vascular pattern, and nuclear architecture that distinguish low-grade (see FIG. 5d) from high-grade (see FIG. 5e-5f) gliomas are apparent as well. Notably, SRH suggests that the perinuclear halos of oligodendroglioma cells (see FIG. 5d), not typically seen on frozen section and thought to be an artifact of fixation, are reflective of abundant protein-rich tumor cell cytoplasm. In addition, by highlighting the protein-rich basement membrane of blood vessels, SRH is well-suited for highlighting microvascular proliferation in high-grade glioma (as shown in FIG. 5f).

Figure 5H:
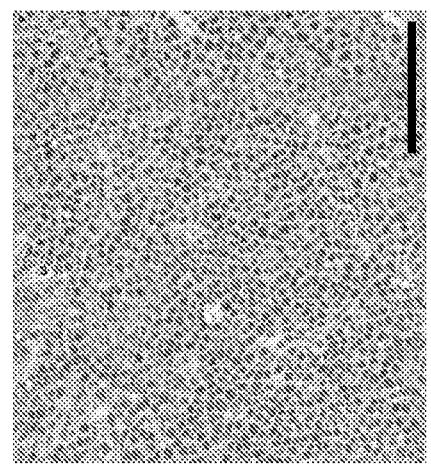
FIG. 5h illustrates a SRH that reveals monomorphic cells of lymphoma with high nuclear:cytoplasmic ratio according to certain aspects of the present disclosure.
Figure 5G:
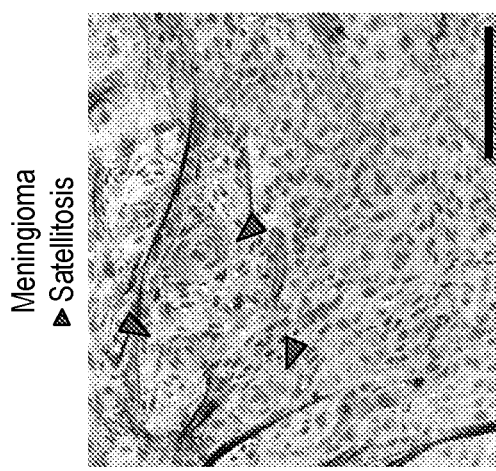
FIG. 5g illustrates a SRH that reveals the whorled architecture of meningioma (black arrowheads) according to certain aspects of the present disclosure.

SRH also reveals the histoarchitectural features that enable diagnosis of tumors of non-glial origin (as shown in FIGS. 5g-5i), including the whorled architecture of meningiomas (see FIG. 5g), the discohesive monomorphic cells of lymphoma (see FIG. 5h), and the glandular architecture, large epithelioid cells, and sharp borders of metastatic adenocarcinoma (see FIG. 5i). SRH is also capable of visualizing morphologic features that are essential in differentiating the three most common pediatric posterior fossa tumors—juvenile pilocytic astrocytoma, medulloblastoma, and ependymoma—each of which have divergent goals for surgical management. In pilocytic astrocytomas, SRH detects piloid (hair-like) architecture and Rosenthal fibers, which appear dark on SRH due to their high protein content. SRH also reveals the markedly hypercellular, small, round, blue cell appearance and rosettes in medulloblastoma, as well as the monomorphic round-to-oval cells forming perivascular pseudorosettes in ependymoma.

SRH may also be utilized in the detection of intratumoral heterogeneity. Gliomas often harbor histologic heterogeneity, which complicates diagnosis and treatment selection. Heterogeneity is particularly common in low-grade gliomas suspected of having undergone malignant progression, and demonstration of anaplastic transformation is essential for making a diagnosis. SRH may be utilized in detecting heterogeneity of tumor grade within a specimen collected from a patient with a recurrent oligodendroglioma of the right frontal cortex. In such a specimen, SRH may reveal both low-grade architecture and areas of high-grade architecture characterized by hypercellular, anaplastic, and mitotically active tumor, as shown in FIG. 6a herein.

In other tumors, such as mixed glioneuronal tumors, histologic heterogeneity is a necessary criterion for diagnosis: while any single histopathologic sample may reveal glial or neuronal architecture, the identification of both is necessary for diagnosis. In a patient with suspected ganglioglioma, a glioneuronal tumor, intraoperative SRH images of a superficial specimen (see FIG. 6b) reveals clustered dysplastic neurons, while a deep specimen reveals hypercellular piloid glial architecture. Consequently, by providing a rapid means of imaging multiple specimens, SRH may reveal intratumoral heterogeneity needed to establish clinically relevant variations in both grade and histoarchitecture during surgery.

According to some examples of the present disclosure, the systems and methods described herein may facilitate quantitative evaluation of SRH-based diagnosis. For example, given its ability to reveal diagnostic histologic features, SRH may be utilized to provide an alternative to existing methods of intraoperative diagnosis. To test this hypothesis, specimens are imaged from thirty neurosurgical patients where intraoperative diagnosis is rendered using routine frozen sectioning or cytological techniques. Adjacent portions of the same specimens are utilized for both routine histology and SRH.

To simulate the practice of intraoperative histologic diagnosis, a computer-based survey is created, in which three board-certified neuropathologists, each practicing at different institutions, are presented with SRH or routine (smear and/or frozen) images, along with a brief clinical history regarding the patient's age group (child/adult), lesion location, and relevant past medical history. The neuropathologists responded with an intraoperative diagnosis for each case the way they would in their own clinical practices. Responses are graded based on: 1) whether tissue is classified as lesional or non-lesional, 2) for lesional tissues, whether they have a glial or non-glial origin, and 3) whether the response contains the same amount of diagnostic information (lesional status, grade, histologic subtype) as the official clinical intraoperative diagnosis.

Assessing the pathologists' diagnostic performance when utilizing SRH versus clinical frozen sections reveals near-perfect concordance (Cohen's kappa) between the two histological methods for distinguishing lesional and non-lesional tissues ($\kappa=0.84-1.00$) and for distinguishing lesions of glial origin from non-glial origin ($K=0.93-1.00$) as shown in Table 1 below. Near-perfect concordance also existed between the two modalities in predicting the final diagnosis ($K=0.89-0.92$) (see Table 1). Inter-rater reliability among reviewers and concordance between SRH and standard H&E-based techniques for predicting diagnosis was also nearly perfect ($K=0.89-0.92$). Notably, with SRH, the pathologists are highly accurate in distinguishing lesional from non-lesional tissues (98%), glial from non-glial tumors (100%), and predicting diagnosis (92.2%). These findings suggest that pathologists' ability to derive histopathologic diagnoses from SRH images is both accurate and highly concordant with traditional histological methods.

TABLE 1

SRH vs Conventional Histology Survey Results

| Specimen Type | Imaging Modality | NP1 Correct | NP1 Incorrect | NP2 Correct | NP2 Incorrect | NP3 Correct | NP3 Incorrect | Combined Accuracy |
|---|---|---|---|---|---|---|---|---|
| Differentiating Non-lesional and Lesional Specimens ||||||||| 
| Normal | SRH | 4 | 1 | 5 | 0 | 5 | 0 | 93% |
|  | H&E | 3 | 2 | 5 | 0 | 5 | 0 | 86% |
| Glial Tumor | SRH | 15 | 0 | 15 | 0 | 15 | 0 | 100% |
|  | H&E | 15 | 0 | 15 | 0 | 15 | 0 | 100% |
| Non-Glial Tumor | SRH | 10 | 0 | 10 | 0 | 10 | 0 | 100% |
|  | H&E | 10 | 0 | 10 | 0 | 10 | 0 | 100% |
| Total | SRH | 29 | 1 | 30 | 0 | 30 | 0 | 98% |
|  | H&E | 28 | 2 | 30 | 0 | 30 | 0 | 97.7% |
| Combined accuracy |  | 90% || 100% || 100% || 95% |
| Concordance (k) |  | 0.84 || 1 || 1 ||  |
| Differentiating Glial and Non-glial Tumors ||||||||| 
| Glial Tumor | SRH | 15 | 0 | 15 | 0 | 15 | 0 | 100% |
|  | H&E | 15 | 0 | 15 | 0 | 15 | 0 | 100% |

TABLE 1-continued

| | | | | | | | | |
|---|---|---|---|---|---|---|---|---|
| Non-Glial Tumor | SRH | 10 | 0 | 10 | 0 | 10 | 0 | 100% |
| | H&E | 10 | 0 | 10 | 0 | 10 | 0 | 100% |
| Total | SRH | 25 | 0 | 25 | 0 | 25 | 0 | 100% |
| | H&E | 25 | 0 | 25 | 0 | 25 | 0 | 100% |
| Combined accuracy | | 100% | | 100% | | 100% | | 100% |
| Concordance (k) | | 1 | | 1 | | 1 | | |
| Differentiating Diagnostic Subtypes | | | | | | | | |
| Normal | SRH | 4 | 1 | 5 | 0 | 5 | 0 | 93% |
| | H&E | 3 | 2 | 5 | 0 | 5 | 0 | 86% |
| Glial Tumor | SRH | 14 | 1 | 12 | 3 | 13 | 2 | 86.6% |
| | H&E | 14 | 1 | 14 | 1 | 15 | 0 | 95.5% |
| Non-Glial Tumor | SRH | 10 | 0 | 10 | 0 | 10 | 0 | 100% |
| | H&E | 10 | 0 | 9 | 1 | 10 | 0 | 96.6% |
| Total | SRH | 28 | 1 | 27 | 3 | 28 | 2 | 92.2% |
| | H&E | 27 | 3 | 28 | 2 | 30 | 0 | 94.4% |
| Combined accuracy | | 91.6% | | 91.6% | | 97% | | 94% |
| Concordance (k) | | 0.924 | | 0.855 | | 0.923 | | |

Although both methods are highly accurate in predicting diagnosis, six of the SRH-based diagnostic discrepancies occurred in the classification of glial tumors, as shown in Table 1 above and FIG. 7c.

With brief reference to FIGS. 7a-7c, FIGS. 7a-7c illustrate the simulation of interoperative histologic diagnosis with SRH. More specifically, FIGS. 7a-7c illustrate, among other things, SRH and H&E preparations for six examples of portions of specimens presented in the survey: gliotic brain tissue, medulloblastoma, anaplastic astrocytoma, meningioma, glioblastoma and metastatic carcinoma (scale bars=50 μm).

In three separate instances, pathologists are able to correctly identify a specimen as being glioma, but did not provide a specific grade. Two specimens classified as "Glioma" with SRH are classified as "High-Grade Glioma" with H&E based techniques. High-grade features in gliomas include: significant nuclear atypia, mitotic activity, microvascular proliferation and necrosis. Assessment of nuclear atypia and mitotic figures is subjective and requires ample expertise based on review of hundreds of cases to set up a threshold of "normal" vs atypical morphology in a specimen. Given the subtle difference in appearance of nuclear architecture in H&E and SRH, pathologists may have been more conservative in terms of rendering atypical and mitotic attributions to tumor cells with SRH.

Differences in tissue preparation between conventional techniques (i.e., sectioning) and SRH (i.e., gentle squash) result in differences in the appearance of vascular architecture. Microvascular proliferation is defined as intraluminal endothelial proliferation (several layers of endothelial cells in a given vessel) and is essential in grading gliomas at the time of intraoperative consultation. This can be easier to observe when tissue is sectioned and analyzed in two dimensions. In contrast, while SRH is able to highlight basement membranes, in some cases, it may not reveal the classic architectural features of microvascular proliferation.

Undersampling from specimens may have also contributed to the discrepancies observed. In three survey items, pathologists misdiagnosed ependymoma as "pilocytic astrocytoma" or gave a more general description of the tumor as "low-grade glioma" using SRH images. Ependymomas and pilocytic astrocytomas may have similar nuclear morphology of monotonous elongated nuclei embedded in a background composed of thin glial processes (piloid-like). In the absence of obvious perivascular pseudorosettes, ependymal rosettes or hyalinized vessels, which are not obvious in the survey items, and may be unevenly distributed throughout a tumor, it is understandable that an ependymoma could be misclassified as a pilocytic astrocytoma. Given the concordance of SRH-images with traditional H&E images in the patients, without limiting the disclosure to any particularly theory, it is hypothesized that these errors might have been avoided if larger specimens are provided to reviewers.

The systems and methods described herein also may be utilized to perform machine learning-based tissue diagnosis. Intraoperative image data that is most useful for clinical decision-making is that which is rapidly obtained and accurate. Interpretation of histopathologic images by pathologists is labor and time-intensive and prone to inter-observer variability. Consequently, the systems and methods described herein—which rapidly deliver prompt, consistent, and accurate tissue diagnoses—are greatly helpful during brain tumor surgery. While tumor infiltration can be predicted by quantitative SRS images through automated analysis of tissue attributes, the present disclosure contemplates that a more robust computational processing, as set forth below, may be employed to predict tumor diagnostic class.

Specifically, according to some examples, a machine learning process called a multilayer perceptron (MLP) is presented for diagnostic prediction because it is 1) easy to iterate, 2) easy to verify, and 3) efficient with current computational power. To create the MLP, 12,879 400×400 μm SRH FOVs are incorporated from patients. According to one example, WND-CHRM (which that calculates 2,919 image attributes for machine learning) or the like, may be employed to assign quantified attributes to each FOV. Normalized quantified image attributes may be fed into the MLP for training, iterating until the difference between the predicted and observed diagnoses is minimized, as described in additional detail below. While reference is provided to MLP, it is readily understood that the techniques described herein are applicable to other types of machine learning algorithms.

According to some examples, the MLP may be programmed with two software libraries: Theano and Keras. However, the foregoing libraries are merely exemplary in nature and other suitable software libraries (e.g., tensorflow, caffe, scikit-learn, pytorch, MXNet and CNTK) may be employed as part of MLP without deviating from the teachings herein. Theano is a high-performance low-level mathematical expression evaluator used to train the MLP. Keras is a high-level Python framework that serves as a wrapper for Theano, allowing rapid iteration and testing of different MLP configurations.

According to some examples, the MLP described herein is designed as a fully-connected, 1,024-unit, one hidden layer, neural network. In one example, the network includes eight sequential layers in the following order: 1) dense input layer with uniform initialization; 2) hyperbolic tangent activation layer; 3) dropout layer with dropout probability 0.2; 4) dense hidden layer with uniform initialization; 5) hyperbolic tangent activation layer; 6) dropout layer with dropout probability 0.2; 7) dense output layer with uniform initialization; and 8) a softmax activation layer corresponding to the number of classifications. Other implementations are also envisioned by this disclosure.

Training of the MLP may be, according to some examples, performed using a training set that is exclusive from the survey test set. Loss may be calculated using the multiclass log-loss strategy. The selected optimizer may include the following parameters: learning rate=0.001, beta 1=0.9, beta 2=0.999, and epsilon=$1 \times 10^{-8}$.

To test the accuracy of the MLP, a leave-one-out approach is utilized, wherein the training set contains all FOVs except those from the patient being tested. This method maximizes the size of the training set and eliminates possible correlation between samples in the training and test sets. The MLP may be configured to make predictions on an individual FOV level, yielding probabilities that a given FOV belongs to one of the four diagnostic classes: non-lesional, low-grade glial, high-grade glial, or non-glial tumor (including metastases, meningioma, lymphoma, and medulloblastoma) (see FIG. 8a). According to this example, the four diagnostic classes are selected because they provide important information for informing decision-making during brain tumor surgery.

To demonstrate, the leave-one-out approach is utilized for the thirty patients that are used in the survey administered to neuropathologists. For each of the thirty patients used to evaluate the MLP, all FOVs (n) from that patient are placed in the test set. The training set is composed of the 12,879-n remaining FOVs. The 12,879 FOVs are screened by a neuropathologist to ensure they are representative of the diagnosis they are assigned to. FOVs are classified as non-lesional, pilocytic astrocytoma, ependymoma, oligodendroglioma, low-grade diffuse astrocytoma, anaplastic oligodendroglioma, anaplastic astrocytoma, glioblastoma, meningioma, lymphoma, metastatic tumor, and medulloblastoma.

The MLP is trained for twenty-five iterations, with the following 26 iteration weights recorded to use for validation of the test set. The test set is fed into each of these 26 weights with the resulting probabilities of each of the 12 diagnostic classes averaged to create a final probability for each diagnosis for each FOV. The 12 diagnoses are condensed to four classes (non-lesional, low-grade glial, high-grade glial, and non-glial) to achieve diagnostic predictions. The low-grade glial category included FOVs classified as pilocytic astrocytoma, ependymoma, oligodendroglioma, and low-grade diffuse astrocytoma. The high-grade glial category included FOVs classified as anaplastic oligodendroglioma, anaplastic astrocytoma, and glioblastoma. The non-glial category included FOVs classified as meningioma, lymphoma, metastatic tumor, and medulloblastoma.

FIGS. 8a-8b illustrate MLP classification of SRH images. In FIGS. 8a-8b, the specimen from patient 87, a low-grade ependymoma, was classified by the MLP as a low-grade glial tumor. In FIG. 8a, probabilities reflect the following: P(NL)=probability of non-lesional; P9LGG)=probability of low-grade glial; P(HGG)=probability of high-grade glial; P(NG)=probability of non-glial. In addition, representative FOVs include a FOV with a small number of ovoid tumor cells (arrowhead) classified as low-grade glioma (top left, orange outline), a FOV with high cellularity with frequent hyalinized blood vessels (arrowheads) classified as non-glial tumor (top right, green outline), a FOV with moderate cellularity and abundant piloid processes (bottom right, yellow outline) classified as a low-grade glioma, and a FOV with higher cellularity and several prominent vessels (arrowheads) classified as high-grade glial tumor (bottom left, blue outline). Scale bars are 100 μm for the individual FOVs and 500 μm for the mosaic image in the center of FIG. 8a.

Given the histoarchitectural heterogeneity of CNS tumors and the fact that some specimens may contain a mixture of normal and lesional FOVs, diagnostic accuracy of the MLP has been judged based on the most common or modal-predicted diagnostic class of FOVs within each specimen (see FIG. 8b). For example, while the specimen from patient 87 exhibited some features of all diagnostic classes in various SRH FOVs (see FIG. 8a), the MLP assigned the low-grade glial category as the highest probability diagnosis in a preponderance of the FOVs (see FIG. 8b), resulting in the correct classification of this specimen as a low-grade glial tumor.

FIG. 9a-9c illustrates MLP-based diagnostic predictions results, where "Y" indicates a correct MLP prediction and "N" indicates an incorrect prediction. The fraction of correct tiles is indicated by the hue and intensity of each heatmap tile, as well as the predicted diagnostic class, where NL=non-legional, LG=low-grade glioma, HGG=high-grade glioma, and NG=non-glial tumor.

To evaluate the MLP in a test set of cases read by multiple pathologists, the leave-one-out approach is applied on each of the thirty cases included in the survey administered to pathologists, as described above. Based on modal diagnosis, the MLP accurately differentiated lesional from non-lesional specimens with 100% accuracy (see FIG. 9a). Additionally, the diagnostic capacity of the MLP for classifying individual FOVs as lesional or non-lesional was excellent, with 94.1% specificity and 94.5% sensitivity. Among lesional specimens, the MLP differentiated glial from non-glial specimens with 90% accuracy at the sample level (see FIG. 9b). The modal diagnostic class predicted by the MLP was 90% accurate in predicting the diagnostic class rendered by pathologists in the setting of the survey (see FIG. 9c).

The cases misclassified by the MLP included a minimally hypercellular specimen with few Rosenthal fibers from a pilocytic astrocytoma (patient 84) classified as non-lesional, rather than low-grade glioma. In this specimen, many of the FOVs resemble normal glial tissue. Another misclassified specimen from a patient with leptomeningeal metastatic carcinoma (patient 72) contained only two FOVs containing tumor. The glioblastoma specimen from patient 82, misclassified as a non-glial tumor by the MLP, contained protein-rich structural elements that resembled the histoarchitecture of metastatic tumors imaged with SRH. Despite these errors, the accuracy and overall ability of the MLP in automated detection of lesional status and diagnostic category provides proof-of-principle for how the MLP could be used for automated diagnostic predictions.

In some embodiments, it follows that the diagnostic module classifies the tissue sample into categories using a neural network, where the neural network is trained with images from predesignated categories. Categories in one example embodiment are illustrated in FIG. 19. In this example embodiment, the diagnostic module classifies the tissue sample into categories which include a tumoral tissue category or a nontumoral tissue category, where the tumoral tissue category is a tissue sample with a tumor and the nontumoral tissue category is a tissue sample without a tumor. The tumoral tissue category further includes a surgical subcategory and a nonsurgical subcategory, where the surgical subcategory indicates the tumor should be removed by surgery and the nonsurgical subcategory indicates the tumor should not be removed by surgery. The surgical subcategory includes a subcategory for glial tumors and a subcategory for nonglial tumors. The subcategory for nonglial tumors may further include subcategories for schannoma tumors, meningioma tumors, metastatic tumors, pituitary tumors and medulloblastoma tumors. The subcategory for glial tumors may further include subcategories for glioblastoma tumors and low grade glioma tumors. The nontumoral tissue category includes a subcategory for normal brain tissue and a subcategory for gliosis tissue. The categories may or may not include a non-diagnostic category for images that cannot be categorized. For the non-diagnostic category, the neural network can be trained with images designated as unable to be categorized. These categories are merely illustrative of one implementation and not intended to be limiting.

FIGS. 16 and 17 further illustrate an example method for analyzing SRH images captured by the imaging system 10. As a starting point, an image is received at 161, for example directly from the imaging device. In this case, the image corresponds to the field of view of the imaging device (e.g., 1000×1000 pixels). In another example, the image may be larger than the field of view of the imaging device (e.g., 6000×6000 pixels), where the larger image is stitched together from smaller images captured by the imaging device.

The image is segmented at 162 into two or more strips for subsequent processing. For example, a large image of 6000×6000 pixels may be segmented into six (6) strips of 1000×6000 pixels. In some examples, segmentation is not needed as the two or more strips are received directly from the imaging device. In any case, each strip is retrieved and processed as indicated at 163. It is readily understood that processing and diagnosing of a strip may be performed by a computer processor that is separate and distinct from the computer processor associated with the imaging system. In some instances, the image strips may be transmitted to a remote location for processing as further described below.

For each strip, a diagnosis is computed for the strip as indicated at 164 and further described in relation for FIG. 17. In an example embodiment, the strip is classified by a neural network and the probability for each class in the classification model is returned as the diagnosis. For the first strip, the probability distribution is reported at 167 as the diagnosis for the tissue sample. However, as more data is received (i.e., more strips from the imager), the diagnosis is updated in real-time. To do so, probabilities for subsequent strips are combined at 165 with the probabilities for the current strip. In one example, probabilities within a given class are summed together to form an accumulated probability distribution. The accumulated distribution is normalized at 166 in a manner further described below. The normalized accumulated distribution is then reported as the diagnosis as indicated at 167. The process is repeated for each new strip which comprises the image until no more strips remain as indicated at 168. The assumption is that the distribution is broad when data first becomes available and becomes more pronounced as the image approaches completion, thereby giving surgeons more confidence in the decision.

With reference to FIG. 17, a diagnosis for a strip is performed on a patch-by-patch basis. In the example embodiment, the strip is further segmented into a plurality of patches. For example, a strip comprised of 900×6000 pixels may be segmented into sixty (60) patches, where each patch is 300×300 pixels. Strip and patch sizes are merely illustrative and not limiting.

To compute a diagnosis for the strip, each patch in the strip is first classified at 171 using the neural network. In the example embodiment, the classifier output is for each stored in a N×14 array, where N is the number of patches in the strip and 14 is the number of classes in the classification model. One of the classes is preferably a non-diagnostic class for patches that cannot be categorized. It is envisioned that the neural network is trained with images that are designated as being unable to be classified, for example by a pathologist.

Strips deemed to be non-diagnostic can be filtered. For example, if a majority of the patches which comprise a given strip are classified as non-diagnostic, then the given strip can be discarded at 173 and thus does not contribute to the diagnosis. On the other hand, if less than a majority of the patches which comprise the given strip are classified as non-diagnostic, then processing of the strip continues as indicated at 172.

Next, an assessment is made as to whether the given strip represents normal tissue. In the example embodiment, probabilities across the categories for the given strip are normalized to one. The normalized probabilities for the categories which comprise normal tissue (e.g., grey matter, white matter and gliosis) are summed together and compared to a threshold (e.g., 90%). If the summed probabilities for normal tissue categories exceeds the threshold, the given strip is deemed to be normal tissue and this result is returned at 177. Conversely, if the summed probabilities for the normal tissue categories does not exceed the threshold, then the probabilities for these normal tissue categories are set to zero at 175 and the adjusted probabilities across all of the categories for the given strip are again normalized to one. In this case, these renormalized probabilities are returned as the diagnostic result for the given strip. This is significant because it allows for a more robust statistical analysis of the tissue. Sub-tumor accuracy is improved when a tissue has an aggregate "tumor" diagnosis of 80% and the remaining 20% of "normal" tissue is zero'd out. In some tumor pathologies, a portion of the tissue might have nested tumor on a backdrop of normal tissue. This "re-normalizaton" algorithm will correctly diagnose the nested tumor even though a portion of tissue might be normal. This method for analyzing SHR images is further depicted in the diagram shown in FIG. 18.

Furthermore, pseudo code for an example implementation of this method is set forth below.

```
1:  Inputs
2:      patches (set of arrays): a set of N images rom a patient
3:      model (computational graph): trained CNN
4:
5:  Outputs
6:      distribution (dictionary): a mapping of diagnostic classes to
        probabilities
7:
8:  procedure PREDICTION(patches/model)
9:      predictions ← []
10:     for patch in patches do
```

```
11:    softmax_output ← model(patch)
12.:   if argmax(softmax_output) =="nondiagnostic" then
13:        continue
14:    else
15:        append softmax_output to predictions
16:    return predictions
17:
18:    procedure RENORMALIZE(predictions)
19:        summed_dist ← sum(predictions)
20:        for class in predictions do
21:            predictions.class ← sum(predictions.class)/summed_dist
22:        return predictions
23:
24:    procedure DIAGNOSIS (patches, model)
25:        renorm_prediction ← RENORMALIZE(PREDICTION (patches,
           model))
26:        if sum(renorm_prediction.normal)> 0.9 then
27:            return renorm_prediction
28:        else
29:            renorm_prediction.normal ← 0
30:            return RENORMALIZE(renorm_prediction)
31:
32:    return DIAGNOSIS(patches, model)
```

Accurate intraoperative tissue diagnosis is essential during brain tumor surgery. Surgeons and pathologists rely on trusted techniques such as frozen sectioning and smear preparations that are reliable but prone to artifacts that limit interpretation and may delay surgery. A simplified standardized method for intraoperative histology, as presented herein, creates the opportunity to use intraoperative histology to ensure more efficient, comprehensive sampling of tissue within and surrounding a tumor. By ensuring high quality tissue is sampled during surgery, SRH raises the yield on testing biopsies for molecular markers (e.g. IDH and ATRX mutation, 1p19q co-deletion, MGMT and TERT-promoter alteration) that are increasingly important in rendering final diagnosis. The present disclosure reports the first demonstration of SRS microscopy in a clinical setting and shows how it can be used to rapidly create histologic images from fresh specimens with diagnostic value comparable to conventional techniques.

Fluorescence-guided surgery, mass spectrometry, Raman spectroscopy, coherent anti-Stokes Raman scattering microscopy, and optical coherence tomography, which exploit histologic and biochemical differences between tumor-infiltrated and normal tissues, have been proposed as methods for guiding excision of brain and other types of tumors. To date, however, no microscopic imaging modality tested in a clinical setting has been successful in rapidly creating diagnostic-quality images to inform intraoperative decision-making. Accordingly, the systems and methods herein leverage advances in optics and fiber-laser engineering to provide an SRS microscope that is easy to operate, durable, and compatible with a patient care environment, which rapidly provides diagnostic histopathologic images.

SRH is well-suited for integration into the workflow for brain tumor surgery. A surgical instrument that can simultaneously collect biopsies for SRH and be tracked by a stereotactic navigational system enables the linkage of histologic and positional information in a single display. Integration of SRH and surgical navigation creates the possibility of verifying that maximal safe cytoreduction has been executed throughout a surgical cavity. In situations where tumor is detected by SRH but cannot be safely removed, for example, it may be possible to serve as a way to better focus the delivery of adjuvant therapies.

As medical data become increasingly computer-based, the opportunity to acquire virtual histologic sections via SRS microscopy creates numerous opportunities. For example, in many clinical settings where brain tumor surgery is carried out, neuropathology services are not available. Currently there are 785 board-certified neuropathologists serving the approximately 1,400 hospitals performing brain tumor surgery in the United States. A networked SRS microscope, such as the one disclosed herein, streamlines both sample preparation and imaging and creates the possibility of connecting expert neuropathologists to surgeons—either within the same hospital or in another part of the world—to deliver precise intraoperative diagnosis during surgery.

Computer-aided diagnosis may ultimately reduce the inter-reader variability inherent in pathologic diagnosis and might provide guidance in settings where an expert neuropathologist is not available. For example, and as described herein, machine learning algorithms may be used to detect and diagnose brain tumors. Computer-aided diagnosis in neuropathology has shown promise in differentiating diagnostic entities in formalin-fixed, paraffin-embedded, H&E-stained whole slide images. The computer-aided diagnostic system described herein for intraoperative histology may be configured to reliably predict diagnosis in small fresh tissue samples. The classifier reported herein is capable of distinguishing lesional from non-lesional tissue samples and in predicting diagnostic class based on pooled tile data. According to some examples, a machine learning approach, such as one described herein, may be configured to perform finer diagnostic classification. In addition, the accuracy of diagnostic classifiers, such as those described herein, may also be improved via 1) alternative neural network configurations and systems for convolution; 2) employing feature-based classification; 3) utilizing support vector machines or statistical modeling approaches; and 4) applying rules for data interpretation that account for demographic factors and medical history, as described in further detail below.

As described herein, SRS microscopy can now be utilized to provide rapid intraoperative assessment of tissue architecture in a clinical setting with minimal disruption to the surgical workflow. SRH images may be used to render diagnosis in brain tumor specimens with a high degree of accuracy and near-perfect concordance with standard intraoperative histologic techniques.

According to some examples, generating a virtual H&E image from the 2845 $cm^{-1}$ and 2930 $cm^{-1}$ images acquired from the SRS microscope may utilize a simple linear color-mapping of each channel. After channel subtraction and flattening (described in the following section), a linear color remapping is applied to both the 2845 $cm^{-1}$ and the 2930 $cm^{-1}$ channel. The 2845 $cm^{-1}$ image, a grayscale image, is linearly mapped such that a strong signal in the 2930 $cm^{-1}$ image maps to an eosin-like reddish-pink color instead of white. A similar linear mapping is applied to the 2930 $cm^{-1}$ image with a hematoxylin-like dark-blue/violet color mapped to a strong signal. Finally, these two layers are linearly added together to result in the final virtual-colored H&E image.

The exact colors for the H&E conversion are selected by a linear optimization based on a collection of true H&E-stained slides. An initial seed color is chosen at random for both H&E conversions. The previously described linear color-mapping and addition process is completed with these initial seed colors. The ensuing image is hand-segregated into a cytoplasmic and nuclear portion. These portions are compared with the true H&E images and a cytoplasmic and nuclear hue difference between generated false-colored H&E and true H&E is elucidated. The H&E seed colors are modified by these respective hue differences and the process is repeated until the difference between generated and true images is less than 1% different by hue.

It is possible to generate a virtual-colored H&E image from the SRS images and the acronyms SRS and SRH images consist of the following steps:

1) A mosaic acquisition script is started on the control computer that acquires an (N×N) series of 1024×1024 pixel images from a pre-loaded tissue sample. These images are acquired at the 2845 $cm^{-1}$ and 2930 $cm^{-1}$ Raman shifts and saved as individual two-channel FOVs to a pre-specified folder.

2) The two-channel image is duplicated and a Gaussian blur is applied to the duplicated image. The original two-channel image is then divided by the Gaussian blur to remove artifacts of acquisition and tissue preparation.

3) The 2845 $cm^{-1}$ channel is subtracted from the 2930 $cm^{-1}$ channel in each FOV.

4) New FOVs are created with the 2845 $cm^{-1}$ channel and the 2930 $cm^{-1}$ minus 2845 $cm^{-1}$ channel.

5) The virtual-color H&E script (described in the above section) is run to create an H&E version of the subtracted and flattened tile.

6) The original tile is stitched as previously described. The user is presented with an option to re-stitch with different stitching parameters if the initial stitch produces an unacceptable image. Upon successful stitching, a layout file is generated from the terminal positions of the individual tiles in the stitched image.

7) The virtual-color H&E images are stitched using the layout file generated in step #6, a significantly faster process than re-computing the stitching offsets and merges from scratch.

According to one example, a process for convert a raw SRH image to a probability vector for each of the diagnoses may be performed as follows: 1) use FIJI to subtract the $CH_2$ layer from the $CH_3$ layer and flatten the image as described in the subsection "Tissue Collection and Imaging"; 2) use FIJI to split the two-channel image into a separate $CH_2$ layer and a $CH_3$—$CH_2$ layer; 3) for each of the previous tiles, create 4 duplications of the tile with 90-degree rotations ("rotamers"); 4) use WNDCHRM or the like to generate signature files for each of the tiles from the previous step; 5) normalize the signature files such that all of the feature values are uniformly and linearly mapped to the range (−1.0, 1.0); 6) ($CH_2$) for each of the tiles that correspond to $CH_2$-channel tiles, run the MLP as described above; 7) ($CH_2$) gather all of the rotamers for a given tile and average (arithmetic mean) the prediction values from them to create one consolidated diagnosis-probability vector for a given $CH_2$-channel tile; 8) repeat steps 6-7 for the $CH_3$—$CH_2$ channel; 9) for a given tile, compare the $CH_2$-channel and the $CH_3$—$CH_2$ channel and discard the diagnosis-probability vector for the tile that has a lower maximal probability value; and 10) for a case-by-case diagnosis, group all of the tiles for a case, remove any tile that doesn't have a diagnosis probability of >0.25, and diagnose the case with the most prevalent (mode) diagnosis among the set of tiles. This process is merely illustrative and not intended to be limiting.

Turning now to FIG. 10, a comparison of label-free, unprocessed SRH and conventional H&E stained frozen sections is provided. As shown, SRH images retain the diagnostic histoarchitectural features seen with conventional frozen sections while adding unique features such as axons (white linear structures in anaplastic astrocytoma specimen) that would not be seen in H&E stained tissue. Scale bars are 50 μM in FIG. 10.

In addition to the advantages of SRH imaging and analysis techniques discussed above, the SRH imaging and analysis techniques described herein may offer the following additional benefits. Specifically, SRH images: 1) can be easily obtained using fresh, unprocessed surgical specimens; 2) have diagnostic content comparable to conventional histologic images (see FIG. 10): accuracy exceeded 92% for both SRH and conventional histologic images in a head-to-head comparison. Concordance between conventional histology and SRH was nearly perfect at κ>0.89; 3) are rapidly available in the operating room: diagnostic images are obtained in several minutes (rather than 30-45 minutes, which is the typical turnaround for intraoperative diagnosis at our institutions); 4) preserve tissue for secondary analysis: tissue that has been imaged with SRH retains its structural and biochemical integrity and is suitable for H&E, IHC analysis and sequencing; 5) can be easily uploaded to a hospital picture archiving and communication system (PACS), integrated into the medical record and viewed via existing PACS viewers. The capacity for uploading and transferring images unlocks the possibility for remote interpretation, connecting centers with scarce neuropathology resources to well-staffed centers and provides a more streamlined workflow for intraoperative diagnosis; 6) are quantifiable allowing for automated image classification and diagnosis.

If broadly applied in the discipline of brain tumor surgery, as well as the larger field of surgical oncology, SRH stands to impact the surgical care of cancer patients by improving efficiency in the operating room by reducing the time spent waiting for diagnosis. The speed at which SRH images are obtained creates an opportunity to expand the use of histologic data to drive better surgical decision-making. For example, through SRH, neurosurgeons may verify the tumor content of the tissues at resection cavity margins. Depending on the clinical scenario, further surgery, targeted postoperative radiation or local chemotherapy may be carried out where SRH-detectable tumor is detected.

Notably, SRH has potential applications in other disciplines of surgical oncology where intraoperative diagnosis and tumor detection is essential. For example, Stimulated Raman Scattering Microscopy may also be suitably applied to detection of tumor in head and neck surgical specimens, as well as the fields of breast cancer surgery and thoracic oncology. Finally, the quantifiable nature of SRH images creates an avenue for applying advances in artificial intelligence and computer-based image classification to assist in tumor detection and diagnosis.

In many clinical settings where brain tumor surgery is carried out, expert neuropathology services are not available. Without a reliable means for establishing intraoperative diagnosis, it can be challenging to deliver the best possible care to brain tumor patients. Artificial intelligence (AI)-based systems for histopathologic diagnosis of neoplasms has been proposed since the practice of pathologic diagnosis relies heavily on pattern recognition, a task to which computers are well suited. AI, including AI-based systems and methods disclosed herein, may be utilized to assist pathologists, especially those without formal subspecialty training in neuropathology, to render accurate tissue diagnoses.

In the era of molecular diagnosis, classifying tumors based on morphology alone is increasingly insufficient for rendering final diagnosis. Nonetheless, the vast majority of relevant intraoperative questions that inform surgical decision-making can be answered by evaluating tissue morphology and cytology alone. Specifically, tissue morphologic features can differentiate lesional from non-lesional tissue, ensuring tissue collected will be useful for rendering final diagnosis and in differentiating lesions that should be surgical removed (gliomas, metastases) from those that should not (lymphoma and germinoma). Image classification based on morphologic features is an area of computer science that has burgeoned as computing power and advances in artificial intelligence have occurred.

According to certain examples of the present disclosure, automated image analysis may be linked with artificial intelligence to deliver diagnostic classification during surgery. Preliminary data demonstrate the feasibility of employing image quantification and AI to answer key questions that dictate surgical strategy during brain tumor operations. It has been demonstrated that SRH image attributes (i.e., cellularity and axonal density) are quantifiable and create a basis for detecting the presence of tumor, even in areas that appear grossly normal. In addition, comprehensive qualitative image analysis may be employed incorporating 2,919 image attributes into a multi-layer perceptron capable of differentiating: (1) lesional from non-lesional specimens with 100% accuracy, (2) glial from non-glial tumors with 90% accuracy and (3) amongst non-lesional tissue, low-grade glial tumors, high grade glial tumors and non-glial tumors with 90% accuracy, as shown in FIGS. 9a-9c.

Referring now to FIG. 11, a comparison of the workflow for conventional histology with a workflow for SRH image generation according is provided. As shown in FIG. 11, SRH may be utilized to streamline and accelerate the current practice of intraoperative histology by eliminating the time and resources inherent in conventional techniques. The central advantage of SRH is the straightforward process for acquiring histologic images as described in FIG. 11. While conventional techniques require 7-10 processing steps, involving toxic chemicals that must be carried out in a regulated, dedicated pathology lab, SRH can be executed in three simple steps, all of which may be executed within the operating room in a matter of minutes.

By streamlining the practice of intraoperative histology, clinical care of cancer patients would be improved in the following ways: 1) reduced downtime in the operating room while an intraoperative diagnosis is established; 2) reliance on a protocol for preparing tissue that is less prone to error and more uniform across a range of specimens; 3) reliance on a tissue preparation protocol that does not introduce freezing artifact and preserves tissue and cellular architecture; 4) establishing a straightforward way for pathologists to review diagnostic histologic images and communicate findings with surgeons—both within a hospital and between hospitals; and 5) providing a central data repository of intraoperative pathology data that could be used to develop and test AI approaches to assist in diagnosis.

In addition to the foregoing benefits, SRH offers other benefits as well. For example, SRH is (i) free of reliance on dyes and (ii) can be carried out under ambient lighting conditions common in the operating room. Both of these properties help ensure that SRH can be successfully carried out by the surgical team in the operating room with minimal disruption of the existing workflow. SRH has the added benefit of leaving imaged tissue, entirely unperturbed. Because tissue is not labeled in any way, it can be used later for routine H&E staining, histochemical analysis and sequencing. Further still, despite the existence of other techniques for histology, only SRH has been demonstrated to have the ability to combine intrinsic chemical contrast and sub-micron spatial resolution to reveal the histomorphologic cues that enable rapid cancer detection and diagnosis.

The industry standard for storage of medical images is via DICOM format. DICOM images are typically stored on PACS. A pathway has previously been established for the conversion of SRH images into DICOM format, as well as storage of SRH images on hospital PACS systems that can be accessed via a web-based DICOM viewer though a link from a hospital electronic medical record. However, with conventional systems and methods, it was not possible to record comments, diagnoses or annotate images.

Accordingly, one aim of the systems and methods described herein is to provide a high-speed pathway by which small packets of information may be transferred within a hospital network from a pathologist's workstation to the SRH imager in the operating room to, among other things, promote collaboration between surgeons and pathologists during SRH image review. In this way, a pathologist utilizing the systems and methods of the present disclosure may manipulate (pan, zoom) a SRH image on a SRH imager in the operating room and use a visible cursor or static animation tools to annotate key features within the images. This may allow the pathologist to demonstrate to the surgeon exactly why he or she has arrived at a given diagnostic conclusion, with the advantage that the pathologist has no need to come to a frozen section lab to review slides and the surgeon has no need to leave a patient in the operating room to review slides and discuss diagnosis with the pathologist.

Turning now to FIG. 12, one example of a system for enabling bidirectional transfer and annotation of SRH images is shown (e.g., a network architecture). The system may facilitate a virtual collaborative space linking SRH imaging systems in operating rooms to pathologists through a centralized image data center. Specifically, the system may include an imaging subsystem residing in the operating room and an image interpretation subsystem located remotely from the operating room. The imaging subsystem captures images of a tissue sample in the manner described above. A communication device is interface with the imaging subsystem and operates to transmit the images over a network to the image interpretation subsystem. The image interpretation subsystem in turn operates to display the images of the tissue sample. In some embodiments, it is envisioned that the image interpretation subsystem further includes the diagnostic module which also operates in the manner described above.

According to some examples, the system may operate as follows. Unrestricted communication between neurosurgeons and neuropathologists aides in establishing a preliminary diagnosis and creating a treatment plan during brain tumor surgery. However, the physical separation between the operating room and the frozen section lab, coupled with the time required for slide preparation, may impede free communication about tissue diagnosis between neurosurgeons and neuropathologists during surgery. For example, it can be difficult for surgeons to leave the operating room to meet with a neuropathologist and review slides in a frozen section lab during an operation. It can also be difficult for pathologists to supervise and make diagnoses in multiple frozen section laboratories across a medical campus, adding to the time required to provide guidance to surgeons.

Accordingly, in conjunction with collaboration system described herein and shown in FIG. 12, large image datasets may be executed through hospital PACS systems according to established DICOM communications protocols. Real-time collaboration may be executed through a separate communications channel that goes beyond DICOM, and allows high-speed and bi-directional communication of meta-data (e.g. real-time imaging pan/zoom or annotation).

Two exemplary challenges facing implementation of communication pathways between SRH imagers, a PACS archive, and pathologist workstation include: (1) ensuring the data integrity and (2) providing real-time collaboration for fairly large datasets (100's of MB). To address these challenges, the architecture described herein and shown in FIG. 12 facilitates data exchange through hospital PACS systems according to established Digital Imaging and Communications in Medicine (DICOM) communications protocols to ensure the robustness of communication of large medical image datasets (originally designed for large MRI 3D image data-sets) and a secondary communication pathway through peer-to-peer communication, established between the surgeon and pathologist for real-time collaboration. In this architecture, the functionality of the existing Graphical User Interface (GUI) of the Imager may be expanded upon for surgeons and include a novel image viewer for the pathologists.

According to one implementation of the present disclosure, systems and methods for optimizing a SRH imager graphical user interface (GUI) are provided. In addition, the present disclosure provides a SRH image viewer with rapid, DICOM compliant up- and download capability for transferring SRH images to and from a PACS archive. According to one example, DICOMIZER software from H.R.Z. Software Services LTD or the like may be utilized to convert SRH images to DICOM format. The converted SRH images may be uploaded to a PACS system (e.g., a hospital PACS system), and accessed via, for example, Epic image viewer or the like linked to the electronic medical record. In this manner, this capability may be integrated in the GUI of the SRH imaging system, such that upload is started automatically while image acquisition is executed. SRH images can be fairly large (100 MPixel in RGB, i.e., about 300 Mbyte) but the acquisition rate (~1 Mbyte/s) is slower than the typical hospital intranet speed. Thus, by starting the upload in parallel to the image acquisition, minimal latency can be achieved.

Similarly, the present disclosure provides an SRH image viewer for the pathologist that is capable of identifying a study on the PACS system and downloading the images. In one example, the SRH image view may be configured to periodically (e.g., constantly) ping the PACS system for novel image data and start downloading the data as it appears from the SRH imaging system. By relying on the stringent DICOM standard for image communication and established PACS system, data integrity may be ensured.

According to other implementations of the present disclosure, an interface for a bi-directional pathway for annotation of SRH images allowing for rapid collaboration is provided. While PACS systems are designed for hosting large image data, they are not designed for rapid collaboration. During the reading of a frozen section, a pathologist will often demonstrate areas with diagnostic histoarchitecture supporting their favored diagnosis. Accordingly, one aim of the present disclosure is to provide a fast (no perceived latency) pathway allowing a pathologist to review images, insert annotations into the image metadata and edit a form containing a free text field for recording the diagnostic impression. All annotations and rendered diagnoses may be visible in the operating room on the SRH imager where tissue is imaged.

Applying the systems and methods disclosed herein, surgeons awaiting pathology results will be notified in the operating room in real-time when an annotated image and/or diagnosis is available. The key realization is that the raw image datasets are already present on both the Imager and the Viewer through the PACS communication and it is only necessary to communicate current image coordinates, zoom-level and annotations rather than full HD images, which are very low data volume (e.g., a few bytes). According to one example, the Imager GUI and the Imager Viewer described herein may be equipped with a peer-to-peer direct communication protocol for image meta-data, such as annotation or image coordinate/zoom.

According to some examples, following implementation of the systems and techniques described herein, pathologists may view uploaded SRH images within 1 minute of acquisition and surgeons may view annotations by the pathologist in SRH images without perceived latency.

Turning now to FIG. 13, a flowchart illustrating method for performing diagnosis using pooled SRH and conventional histology images is provided. By conducting SRH diagnosis in conjunction with conventional histology diagnosis by a study pathologist and/or clinical diagnosis by a consulting pathologist, the accuracy of a given diagnosis may be improved.

Turning now to FIG. 14, a diagram illustrating stitched image acquisition according to one example implementation is provided. Stitched image acquisition may be carried out as part of, or in conjunction with, the bi-directional communication pathway for annotation of SRH images allowing for rapid collaboration described herein.

More specifically, and with continued reference to FIG. 14, a system for acquiring, transmitting and displaying intra-operative histology images in accordance with aspects of the present disclosure is described.

Because surgeons are not always experts in pathology, they rely on dedicated pathologists for intra-operative consultations. In the current clinical practice, tissue is biopsied and transported to the frozen section lab for processing. Pathologists come to this lab for interpretation of the stained tissue section and call the surgeons with the results. An alternative intra-operative histopathology (Stimulated Raman Histology (SRH)) analyzes fresh tissue specimens in the operating room (OR) or in an adjacent core laboratory that serves multiple ORs. Pathologists do not typically come to the OR, as it is time-consuming to enter a sterile environment, and in many institutions, pathologists are in a different part of the hospital. In some cases, surgery is performed in satellite settings or hospitals that do not have dedicated pathology staff.

Transferring images from the imager to the interpretation station in digital format is therefore needed. One of the key features of an intra-operative histopathology imaging system is time-to-diagnosis, as OR time is expensive; it is generally desirable to minimize time under anesthesia, and long wait-times for diagnosis inhibits using pathology as a means for mapping the surgical cavity for residual tumor. As such it is desirable to minimize transfer times of the image data.

Pathology imaging data is known to be very large since millimeter to centimeter size tissue specimen are scanned with high resolution and stitched. The size of a single field of view (FOV) depends on the magnification of the objective lens and the sampling, but is typically about 500 μm×500 μm and scanning a 5 mm×5 mm tissue area requires stitching of 100 FOVs. Typically, individual FOVs have 1 to 5 MPixel (i.e. 3-15 MB in 8-bit RGB mode), and a stitched image would thus be 300 MB to 1.5 GB and image transfer alone can take many minutes. Advanced methods use strip-tiling where a line image is acquired while the motorized stage moves in an orthogonal direction to acquire a FOV in the form of an image strip with a length that is independent of the objective length. While such an approach reduces the number of FOVs that need to be stitched, it does not reduce the data size.

FOVs are subsets of a larger image of a tissue specimen that may or may not have some overlap with neighboring FOVs. In some cases, FOVs may be stitched to provide a larger image of a tissue specimen. FOVs can be separately interpreted, saved or transferred to a remote storage, interpretation or viewing station. The nature of a FOV may be related to how images are acquired. In one example, images are acquired by means of strip-tiling, whereby an image is scanned by a 1-axis scan-mirror or a line-camera and a motorized-stage moves the sample in a more or less perpendicular direction to acquire an image strip over time. In this case, a FOV would be a rectangular strip. In another example, a strip may be artificially subdivided into subsections, each of which may be its own FOV. In yet another example, images are acquired by using a 2-axis scanner or a 2D camera. In such an example, a FOV may be the output from this 2D scan or image. In other examples, such a 2D scan or image may be sub-divided into subsections, each of which may be its own FOV. Such sub-divided FOVs may be smaller in size.

Existing digital pathology systems treat image acquisition, transfer and display as independent systems. The acquisition system completes the scanning and stitching of the image and transfers it as a whole. This helps ensure data integrity of medical images. Compression algorithms are often used to reduce the data size, but those can compromise image quality in an unpredictable fashion, which is not desirable for medical image data.

Accordingly, the present disclosure provides an alternative system architecture whereby FOVs are transmitted as partial images, and stitching and displaying of the combined image is performed by the viewing system based on an identification tag that represents, for example, the order of acquisitions that can be correlated to a location of the strip in the image based on a shared setting between the acquisition system and viewing system. With this approach, the image transfer can be started as soon as a partial image has been acquired by the imaging system rather than waiting until all the partial images have been acquired and stitched.

In one example, the data transfer may be peer-to-peer, such that the imaging instrument is directly connected to the interpretation station. In other examples, the connection may include one or more intermediaries. For example, in some implementations (such as the implementation shown in FIG. 12) the imaging instrument may communicate with the image interpretation station through a PACS (which may be implemented, in some examples, as one or more server computers). In the latter case, image upload and download to and from the PACS system may be based on partial image data and assembly of a combined image may performed by the viewing system.

Typically, medical image data complies with the DICOM standard for storage and transfer of imaging files. According to some examples, the approach described herein can be adapted to work within this framework. At the beginning of an image acquisition, a new series may be generated at the PACS system or the viewing system and partial images may be transferred via a network. In some examples, a DICOM tag may be utilized that is integrally associated with the image data to automatically associate a partial image with a particular location in the sample. Such a tag can be an actual position (e.g., representing the center position of the partial image) or it can be an abstract number that can be correlated to an actual position based on knowledge of the acquisition protocol. The viewing system may then receive and download such partial images into a combined image. It may wait until the entire acquisition is complete, or start to display partial image data as it become available. Images may be acquired at neighboring or overlapping location and the viewing system may start amending the combined image, or it can be from separate locations that only provide a complete image after the entire image is assembled.

One advantage of DICOM is that it is compatible with existing hospital IT infrastructure. It shall, however, be noted that concepts and examples described herein may be independent from DICOM image storage and transmission protocols and can be applied to any image data format (e.g., *.jpg, *.tiff, *.bmp, etc.) known in the art. This is particularly true if a dedicated SRGH intra-operative pathology solution is offered that includes one or more of the image acquisition system, data-storage solution, and/or viewing station. In such a scenario, it may be advantageous to utilize a data format or transmission protocol other than DICOM.

In many applications, it is advantageous to acquire partial images that have some degree of spatial overlap and use an overlap algorithm to overlap and merge two neighboring partial images to a combined image (e.g., using cross-correlation and or linear/nonlinear stretching). Such overlapping and merging can be performed either on the imaging acquisition system or the viewing system. In the first case, simple position based stitching of partial images may still be performed by the viewing system, but the data would be organized in such a fashion that the merged part of the overlapped region would only be transmitted with the second partial image.

Some intra-operative histology techniques, including those described herein, may rely on multi-color imaging that is carried out simultaneously or sequentially. Different color channels from the same tissue region can be transmitted either combined in the form of a multi-channel image, or separately as single-channel images. In the latter case, the viewing system described herein may be configured to assemble such images into a multi-channel image.

In some examples, it may be advantageous to perform computer-assisted image interpretation or diagnosis on a computer system that is separate from the computer system that controls the image acquisition. This can be the case if the separate computer system has more computation power than the computer system of the imaging system, such as a hospital based server or a web-based server. The separate computer system can be part of the hospital network or remote. This can also be the case if the computer system of the imaging system shall not be affected by the computational load required by the interpretation such that it can ensure that image acquisition is performed correctly, e.g., if critical timing is required. In such an example, it may be desirable to perform computer-assisted image interpretation or diagnosis on individual FOVs, rather than a complete image and allow for a partial image transfer of individual FOVs. Computer-assisted image interpretation and diagnosis may then be started as soon as the FOVs become available on the separate computer system. A computer system may include a personal computer (PC), server, micro-controller, GPU, or FPGA.

In some examples, the computer system performing the image interpretation or diagnosis may be the same or a different computer system from the computer system that controls the image acquisition, determines when sufficient image data has been acquired to render an image interpretation or diagnosis with sufficient confidence based on the FOVs acquired and interpreted thus far. For example, an overall confidence score for an image interpretation or diagnosis may be generated by combining the image interpretation or diagnosis from individual FOV and applying some weighting, such as the confidence of an individual FOV. Typically acquiring and interpreting more FOVs will result in better overall confidence but it may be the cases that the confidence for a specific image interpretation or diagnosis is above a certain threshold based on one or few FOVs or that the time saved by acquiring and/or interpreting fewer FOVs is more important than an increased confidence level. In part, this may depend on the level of diagnosis needed, e.g. it might be possible to distinguish lesional from non-lesional tissue based on or few FOVs while distinguishing, e.g., glial from non-glial tumor or establishing a full intra-operative diagnosis might require more FOVs to be acquired and interpreted. Based on the desired output and the level of confidence of a correct interpretation of diagnosis for each of these cases, the computer system performing the image interpretation of diagnosis may determine that sufficient FOVs have been acquired and/or interpreted.

In some examples, not every pixel in a FOV may be required to render an image interpretation or diagnosis, and it may be be advantageous to reduce the computation power and/or time by down-sampling. As described in the example below, down sampling from 1000×1000 pixel FOVs or 1024×1024 pixel FOVs to 299×299 pixel FOVs may produce excellent interpretation results while reducing the amount of data by more than 10×. This result is unexpected because, typically, imaging systems for human interpretation strive to provide the best possible image quality, e.g., as measured by resolution and/or sampling density. For example, a costly Olympus 25×1.05NA objective lens with a resolution of <=500 nm and FOV>=500 um may be employed and the acquisition system may acquire>=1000× 1000 pixels such as to sample (or even oversample the optical resolution). However, it may be acceptable to down-sample such images while maintaining acceptable results with computer-assisted image interpretation or diagnosis. Accordingly, the imaging system described herein may be, according to some examples, configured to acquire images with sampling that matches (or oversamples) the optical resolution and then subjects the images to 1D or 2D down-sampling methods such as discrete methods (e.g., pick each third sample) or more advanced methods using interpolation, filtering, convolution, etc. In other examples, the imaging system described herein may be configured to directly produce under-sampled images, e.g., by choosing appropriate sampling rates and/or digital filters in the data-acquisition and/or by choosing asymmetric sampling in the 2D direction (e.g., in the case where images are acquired by means of strip-tiling is might be possible to move the stage in the direction that is essentially perpendicular to the 1D beam-scanned direction at a speed that is faster than what would be required to acquire square pixel). Down-sampling or Under-sampling of FOVs may be used, for example, when image interpretation or diagnosis is performed by the same computer system that controls the image acquisitions, or it may be used in combination with the systems and methods described above where down-sampling is performed prior to transmitting the images to a separate computer system for image interpretation or diagnosis in an attempt to reduce transfer sizes.

In light of the foregoing, according to one example of the present disclosure, a system for acquiring and viewing a magnified image of a tissue specimen is provided. The system may include (i) a microscopy system configured to acquire at least a first partial magnified image at a first location of the tissue specimen and a second partial magnified image at a second location of the tissue specimen; (ii) a first computer system configured to transmit and upload the first and second partial magnified images via a network; and (iii) at least a second computer system configured to receive and/or download the first and second partial magnified images and display (e.g., via a display device included as part of the second computer system) such first and second magnified images as a combined magnified image of the tissue specimen.

In addition to providing a system for acquiring, transmitting and displaying intra-operative histology images, according to some examples in the present disclosure, a system for diagnosing medical conditions based on SRH images using one specific type of machine learning, a convolutional neural network (CNN), is disclosed.

More specifically, one aim of the systems and methods described herein is to provide a CNN for predicting inter-operative diagnosis, i.e., a machine learning-based computational model that accurately classifies intraoperative tissue specimens without human input. This advance, coupled with rapid SRH image acquisition time, may allow a surgeon to obtain key diagnostic information within minutes of obtaining tissue. To effectuate CNN-based diagnoses, the system described herein may account for one or more of image pre-processing (e.g., normalization, augmentation, statistical segmentation, etc.), network structure, size, and output cardinality on CNN diagnostic performance.

In one example, the SRH acquisition process may include sequential imaging of fields of view (FOV) in a mosaic pattern until the entire slide has been imaged. Each FOV may then be stitched to create a complete, high-resolution image of the entire slide. Using a web-based interface, in one example, pathologists may review all FOVs that will be included in the training set, eliminating those where blank space, cautery artifacts, or blood clot predominates.

The remaining FOVs may contain histoarchitectural features that are representative of the frozen section diagnosis (ground truth). Hand-curation allows for high-quality, accurate FOVs to be used for training of the machine learning classifier. In some examples, hand-curated FOVs are not used in the test set. A current dataset of ~450 patients has yielded approximately 1000 slides of tissue and 70,000 FOVs. One example of a SRH data storage and visualization server may include a 4-core 4.0 GHz, 32 GB Memory, 2 TB HDD desktop computer. However, other suitable data storage and visualization computing devices may be equally employed without deviating from the teachings of the present disclosure.

In one example, a random 70%/10%/20% split of patients may be carried out between the training, validation, and test classes, respectively. This split allows a minimum of one patient with each diagnosis to be represented in each class. No patient will have slides and/or FOVs straddling the training/validations/test split.

Acquisition of FOVs with the SRS microscope is a repeatable, stable, and deterministic process. However, to prevent small changes in either tissue or acquisition from biasing the classifier, the present disclosure proposes two pre-processing steps to each FOV prior to inclusion in the rest of the machine learning pipeline: 1) Mean subtraction: Performing a mean subtraction per channel per image allows for the removal of any acquisition artifacts; and 2) Zerocentering and normalization: These allow for the removal of any brightness and contrast differences that may exist between FOVs.

There is no intrinsic rotational or spatial orientation in the acquisition of these images: a neuropathologist can equally make a diagnosis on the image regardless of how the FOV is presented. Using this principle, there are many truth-preserving transforms that can augment a number of unique FOVs for training. With vertical and horizontal mirroring as well as cardinal rotations, a single FOV can generate 16 unique FOVs without obscuring any diagnostic information. This can amplify the training size from 49,000 FOVs (70,000 FOVs*0.7 proportion for training) to 392,000 FOVs (49,000 unique training FOVs*4 rotations*2 mirroring).

According to some examples of the present disclosure, a convolutional neural network (CNN) may be utilized in the diagnosis of FOVs. CNNs constitute a computer vision solution for the translation of raw images into classifications on a distinct set of classes. Several notable CNNs have emerged to solve the problem of real-world object recognition including InceptionV3, InceptionV4, and Xception. According to certain examples, each of these networks may be trained with the FOV training set described above, aiming to optimize accuracy on the validation set and testing on the test set. In order to minimize training time, the pre-trained weights may initially be used from the real-world challenges, also known as transfer-learning. Furthermore, several novel networks may be created based on the CNN operators of convolution, activation, and max-pooling.

In this manner, the systems and methods set forth herein may provide a high-performance CNN that is capable of analyzing FOVs and outputting a probable diagnosis for each FOV. This may facilitate accurate, rapid diagnosis of entire tissue specimens.

Intraoperative tissue often contains a heterogeneous mixture of histoarchitecture that complicate complete specimen diagnosis. Accordingly, one aim of the systems and methods described herein is to use the analyses gathered on individual FOVs to accurately diagnose an entire specimen.

Turning now to FIG. 15, a flowchart illustrating one example method for performing a diagnosis using a CNN is provided. In one embodiment, the diagnostic module generates a secondary diagnosis for the tissue sample by applying a secondary method to the images, for example by determining a quantitative measure of cellularity. For example, in a pipeline parallel to the CNN-based analysis described above, a quantitative analysis of each FOV with an image cytometry tool (i.e., an automated cell image analysis), such as CellProfiler or the like, may be provided. According to some examples, this additional information may be (but need not always be) used to supplement the CNN-based diagnosis for each FOV. In the example embodiment, the diagnostic module outputs a diagnosis when the secondary diagnosis matches the diagnosis for the tissue sample from the machine learning algorithm but otherwise classifies the tissue sample in the non-diagnostic category when the secondary diagnosis does not match the diagnosis for the tissue sample from the machine learning algorithm. It is noted that the secondary method preferably does not use machine learning.

More specifically, neuronal networks are designed to classify an image into a pre-determined category, and it can be difficult predict how failure modes (e.g. use error or hardware failures of the imaging system) may affect the output of the neuronal network. An approach is presented wherein an image is analyzed by two or more independent means which together provide computer-assisted analysis (e.g. convolutional neuronal network to render an intraoperative diagnosis and a cell counter, such as CellProfiler, to generate a measure of cellularity). The final output is only provided if the two means agree by a predefined metric (e.g. diagnosis for "high-grade glioma" is only rendered if cellularity is above a certain threshold, or diagnosis for "normal white matter" requires the cellularity measure to be below a certain threshold). In cases where the independent means do not agree, the final output indicates no classification.

In another feature, the neuronal network can be trained to provide a level of cellularity (e.g. nuclei per sample area). This can be a useful indication because tumors typically have an elevated level of cellularity. While such approaches have been demonstrated to work with regular histology images (e.g. H&E section) or cells/tissue stained with nuclear dyes (e.g. DAPI), this has not been extended to SRH since the image contrast is less specific for nuclei. Specific problems arise from red-blood cells that appear as spherical objects, collagen rich fibers that appear with the same Raman signature as nuclei, and nuclei in white matter tissue that are overwhelmed by the strong Raman signal for myelinated axons. Surprisingly, it has been possible to train a neuronal network to provide a robust measure of cellularity base on SRH images if the appropriated annotated dataset was included in the training set.

With an input of N FOVs that make up an entire slide of tissue, the CNN may provide N vectors of classifications corresponding to the probabilities of each diagnosis. Furthermore, the quantitative image cytometry analysis may provide another N vectors of data describing cell counts, nuclear, and texture characteristics for each FOV. In order to fuse each of these data vectors into a whole-slide diagnosis, a fully connected multi-layer perceptron may be included to translate each of these numerical inputs into a diagnosis. Other techniques that may be incorporated include random forests and statistical, non-machine learning approach based on mean probabilities. The entire workflow for automated diagnosis proposed here is summarized in FIG. 15.

Certain functions ascribed to the systems described throughout the present disclosure, including the claims, may suitably be performed by one or more modules. In the present disclosure, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system, comprising:
an imaging device that captures an image of a tissue sample at an optical section of the tissue sample using Stimulated Raman Scattering, where the tissue sample has a thickness larger than the optical section; and
a diagnostic module configured to receive the image for the tissue sample from the imaging device and generate a diagnosis for the tissue sample by classifying the tissue sample into categories using a convolutional neural network including a tumoral tissue category or a nontumoral tissue category, where the tumoral tissue category is a tissue sample with a tumor and the nontumoral tissue category is a tissue sample without a tumor;
wherein the diagnostic module generates a secondary diagnosis for the tissue sample by determining a quantitative measure of cellularity for the tissue sample and outputs the diagnosis when the secondary diagnosis matches the diagnosis for the tissue sample using the convolutional neural network.

2. The system of claim 1 wherein the imaging device images the tissue sample at a first Raman shift in the range from 2820 cm$^{-1}$ to 2880 cm$^{-1}$, and at a second Raman shift in the range from 2920 cm$^{-1}$ to 2980 cm$^{-1}$.

3. The system of claim 2 wherein the imaging device further images the tissue sample at a third Raman shift in the range from 2750 cm$^{-1}$ to 2820 cm$^{-1}$.

4. The system of claim 1 wherein the tumoral tissue category includes a surgical subcategory and a nonsurgical subcategory, where the surgical subcategory indicates the tumor should be removed by surgery and the nonsurgical subcategory indicates the tumor should not be removed by surgery.

5. The system of claim 4 wherein the surgical subcategory includes a subcategory for glial tumors and a subcategory for nonglial tumors.

6. The system of claim 5 wherein the subcategory for nonglial tumors includes further subcategories for schannoma tumors, meningioma tumors, metastatic tumors, pituitary tumors and medulloblastoma tumors.

7. The system of claim 5 wherein the subcategory for glial tumors includes further subcategories for glioblastoma tumors and low grade glioma tumors.

8. The system of claim 1 wherein the nontumoral tissue category includes a subcategory for normal brain tissue and a subcategory for gliosis tissue.

9. The system of claim 1 wherein the diagnostic module classifies the tissue sample into categories, such that at least one of the categories is a non-diagnostic category for images that cannot be categorized.

10. The system of claim 9 wherein the diagnostic module classifies the tissue sample into categories using a neural network and the neural network is trained with images designated as unable to be categorized.

11. The system of claim 9 wherein the diagnostic module classifies the tissue sample in the non-diagnostic category when the secondary diagnosis does not agree with the diagnosis for the tissue sample from the convolutional neural network, where the secondary method does not use a machine learning algorithm.

12. The system of claim 1 wherein the diagnostic module receives two or more image segments for the tissue sample, generates a diagnosis for each image segment by applying the convolutional neural network to the image segment, and generates a diagnosis for the tissue sample by aggregating the diagnoses for the image segments.

13. The system of claim 12 wherein, for each image segment, the diagnostic module classifies the tissue sample into categories which thereby yields a probability for each category and normalizes the probabilities across the categories to one.

14. The system of claim 13 wherein the diagnostic module generates a diagnosis for the tissue sample by omitting the diagnoses for image segments classified in a non-diagnostic category, where the non-diagnostic category indicates that a given segment cannot be categorized.

15. The system of claim 13 wherein, for the given image, the diagnostic module sets probabilities for any nontumoral tissue categories to zero and renormalizes the probabilities across all of the categories to one, where the nontumoral tissue categories indicate that a tissue sample is without a tumor.

16. A system, comprising:
an imaging device that captures an image of a tissue sample at an optical section of the tissue sample using Stimulated Raman Scattering, where the tissue sample has a thickness larger than the optical section; and
a diagnostic module configured to receive the image for the tissue sample from the imaging device and generate a diagnosis for the tissue sample by classifying the tissue sample into categories using a convolutional neural network including a tumoral tissue category, a nontumoral tissue category and a non-diagnostic category, where the tumoral tissue category is a tissue sample with a tumor, the nontumoral tissue category is a tissue sample without a tumor and the non-diagnostic category is for image that cannot be categorized;
wherein the diagnostic module generates a secondary diagnosis for the tissue sample by applying a secondary method to the image and classifies the tissue sample in the non-diagnostic category when the secondary diagnosis does not agree with the diagnosis for the tissue sample using the convolutional neural network, where the secondary method does not use a machine learning algorithm.

17. The system of claim 16 wherein the imaging device images the tissue sample at a first Raman shift in the range from 2820 $cm^{-1}$ to 2880 $cm^{-1}$, and at a second Raman shift in the range from 2920 $cm^{-1}$ to 2980 $cm^{-1}$.

18. The system of claim 17 wherein the imaging device further images the tissue sample at a third Raman shift in the range from 2750 $cm^{-1}$ to 2820 $cm^{-1}$.

19. The system of claim 16 wherein the diagnostic module receives two or more image segments for the tissue sample, generates a diagnosis for each image segment by applying the convolutional neural network to the image segment, and generates a diagnosis for the tissue sample by aggregating the diagnoses for the image segments.

20. The system of claim 19 wherein, for each image segment, the diagnostic module classifies the tissue sample into categories which thereby yields a probability for each category and normalizes the probabilities across the categories to one.

21. The system of claim 20 wherein the diagnostic module generates a diagnosis for the tissue sample by omitting the diagnoses for image segments classified in a non-diagnostic category, where the non-diagnostic category indicates that a given segment cannot be categorized.

22. The system of claim 21 wherein, for the given image, the diagnostic module sets probabilities for any nontumoral tissue categories to zero and renormalizes the probabilities across all of the categories to one, where the nontumoral tissue categories indicate that a tissue sample is without a tumor.

* * * * *